(12) United States Patent
Yamagata

(10) Patent No.: US 8,852,109 B2
(45) Date of Patent: Oct. 7, 2014

(54) ULTRASOUND IMAGING APPARATUS AND A METHOD FOR GENERATING AN ULTRASOUND IMAGE

(75) Inventor: Hitoshi Yamagata, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1095 days.

(21) Appl. No.: 12/353,482

(22) Filed: Jan. 14, 2009

(65) Prior Publication Data
US 2009/0187104 A1 Jul. 23, 2009

(30) Foreign Application Priority Data
Jan. 23, 2008 (JP) .................................. 2008-012177

(51) Int. Cl.
A61B 8/14 (2006.01)
G01S 15/89 (2006.01)
A61B 8/08 (2006.01)
G01S 7/52 (2006.01)

(52) U.S. Cl.
CPC ............... *A61B 8/483* (2013.01); *G01S 15/892* (2013.01); *G01S 7/52074* (2013.01); *G01S 15/8993* (2013.01); *A61B 8/0833* (2013.01); *G01S 7/52085* (2013.01); *G01S 15/894* (2013.01); *G01S 7/52073* (2013.01); *A61B 8/14* (2013.01); *A61B 8/0841* (2013.01)
USPC ............ 600/445; 600/437; 600/440; 600/443

(58) Field of Classification Search
USPC .......................... 600/407, 437, 440, 443–446
See application file for complete search history.

(56) References Cited

U.S. PATENT DOCUMENTS

| 6,245,017 | B1 | 6/2001 | Hashimoto et al. |
| 6,544,175 | B1 * | 4/2003 | Newman ....................... 600/437 |
| 2005/0228280 | A1 * | 10/2005 | Ustuner et al. ................ 600/443 |
| 2006/0241424 | A1 * | 10/2006 | Akiyama et al. .............. 600/437 |

FOREIGN PATENT DOCUMENTS

| JP | 10-277030 | 10/1998 |
| JP | 2000-139906 | 5/2000 |
| JP | 2000-232978 | 8/2000 |
| JP | 2004-141522 | 5/2004 |
| JP | 2005-152346 | 6/2005 |

OTHER PUBLICATIONS

Japanese Office action mailed Aug. 28, 2012 in Japanese Patent Application No. 2008-012177 filed Jan. 23, 2008.

* cited by examiner

*Primary Examiner* — Tse Chen
*Assistant Examiner* — Mark Remaly
(74) *Attorney, Agent, or Firm* — Oblon, Spivak, McClelland, Maier & Neustadt, L.L.P.

(57) ABSTRACT

A controller makes a scan part scan a three-dimensional first scanning region so as to acquire volume data in the first scanning region and makes the scan part to consecutively scan a second scanning region that is smaller than the first scanning region and is included in the first scanning region more than once so as to consecutively acquire the volume data in the second scanning region. An image generator generates ultrasound image data in the first scanning region including the second scanning region based on the volume data in the first scanning region. Further, the image generator generates new ultrasound image data by updating the volume data in the second scanning region every time volume data in the second scanning region is acquired. The display controller causes a display to update and causes to display an ultrasound image every time new ultrasound image data is generated.

17 Claims, 10 Drawing Sheets

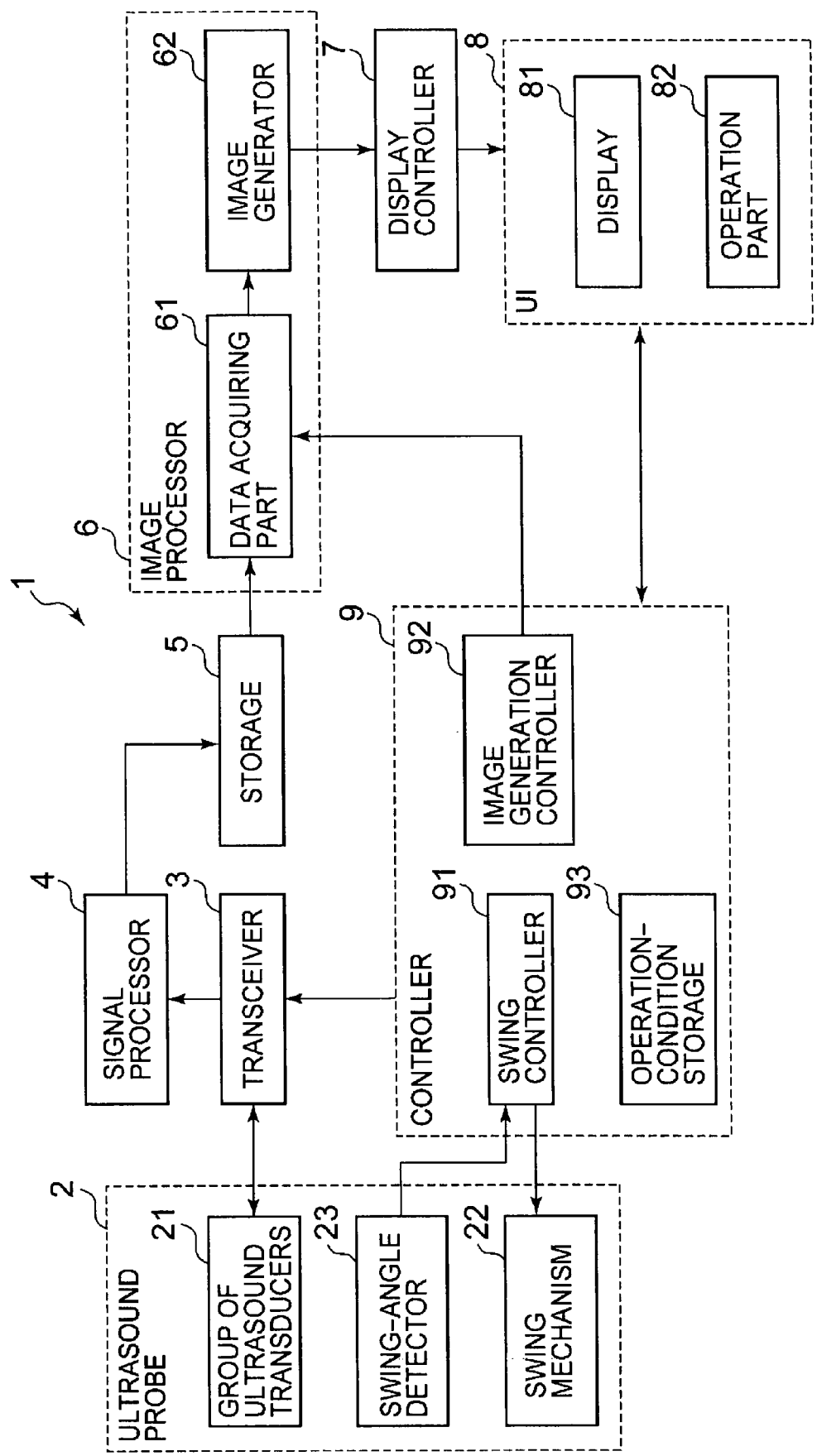

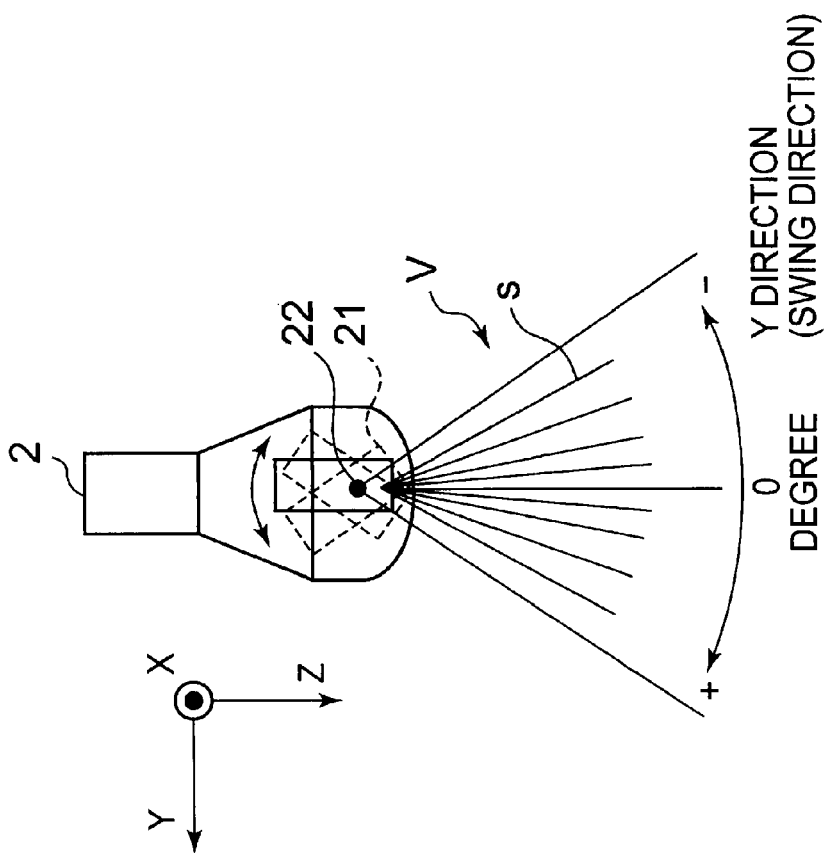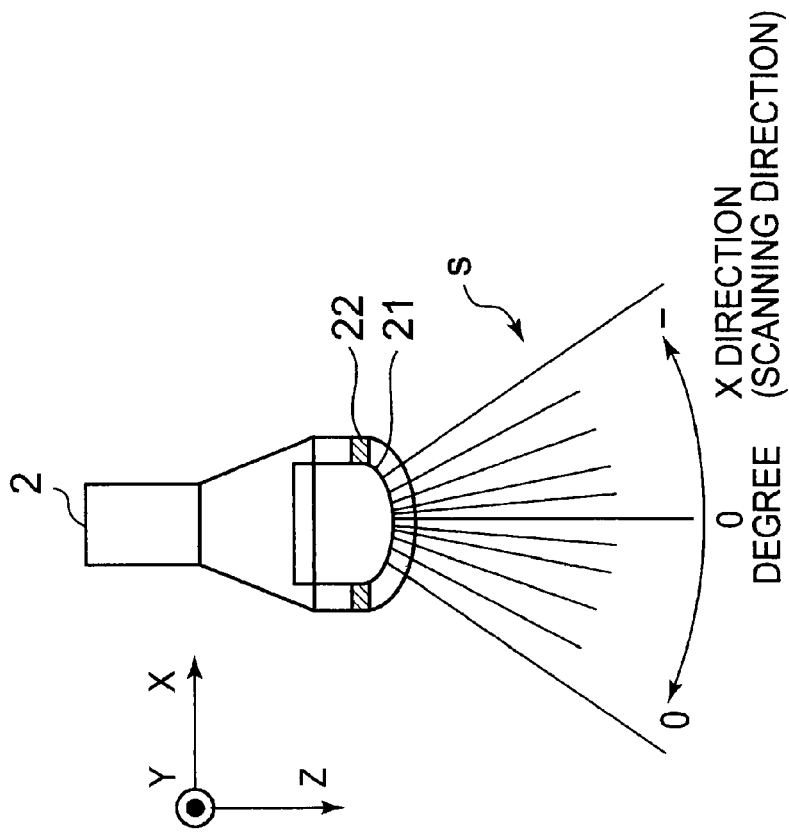

ULTRASOUND IMAGING APPARATUS AND A METHOD FOR GENERATING AN ULTRASOUND IMAGE

BACKGROUND OF THE INVENTION

1. Field of the Invention

The present invention relates to an ultrasound imaging apparatus that scans a three-dimensional region and a method for generating an ultrasound image.

2. Description of the Related Art

Liver cancer accounts for approximately 10% of all cancer diseases, and the number has increased. A medical imaging apparatus such as an ultrasound imaging apparatus, an MRI apparatus and an X-ray CT apparatus is used for diagnosis of liver cancer. In particular, the diagnostic ability has increased in comparison with diagnosis with a two-dimensional image, because the thee-dimensional imaging method has been established in an X-ray CT apparatus and an MRI apparatus.

A method for treatment of liver cancer includes anticancer drug injection into hepatic artery, transcatheter arterial embolization (TAE), transcatheter arterial chemo-embolization (TACE), minimally invasive treatment, and laparotomy.

Among the abovementioned treatments, the minimally invasive treatment is applied particularly in many cases, because this treatment is technically simpler than the other methods and is less stressful for a patient. The minimally invasive treatment includes percutaneous ethanol injection technique (PEIT) and microwave ablation. These treatments are performed with a puncture. Treatment by the percutaneous ethanol injection technique is performed, while a puncture needle is monitored in real time with an ultrasound imaging apparatus, the position of the puncture needle is tracked and the position of the puncture needle is checked. Recently, as ablation treatment, radio frequency ablation (RFA) is often performed with a single needle or an expandable needle to expand to plural needles.

An ultrasound imaging apparatus capable of imaging a three-dimensional region is used for tracking the position of the puncture needle. In a case where a three-dimensional region is scanned with ultrasonic waves by using a 1D array probe in which a plurality of ultrasound transducers are arranged in a row in a predetermined direction (scanning direction), a 1D array probe provided with a swing mechanism is used (for example, Japanese Unexamined Patent Application Publication No. 2007-21018). The 1D array probe provided with a swing mechanism is capable of mechanically swinging the ultrasound transducers arranged in a row in the scanning direction, in a direction (swing direction) orthogonal to the scanning direction, thereby scanning a three-dimensional region with ultrasonic waves and acquiring volume data. The 1D array probe is provided with a motor for swinging the plurality of ultrasound transducers. The 1D array probe mechanically swings the ultrasound transducers in the swing direction by using the motor, thereby scanning a three-dimensional region and acquiring volume data.

By executing volume rendering on the volume data acquired by scan with ultrasonic waves, it is possible to generate three-dimensional image data representing a tissue within a subject and display a three-dimensional image based on the three-dimensional data. Further, by executing multi planar reconstruction on the volume data, it is possible to generate image data (MPR image data) at an arbitrary cross-section and display an MPR image based on the MPR image data.

In the conventional art, a puncture object (lesion) subjected to ablation treatment by a puncture needle and the puncture needle are included in a three-dimensional region scanned with ultrasonic waves, whereby three-dimensional image data representing the puncture object and the puncture needle is acquired. With reference to the three-dimensional image, the operator confirms the position of the puncture needle with respect to the puncture object and observes a process of puncture by the puncture needle.

In order that both the puncture object and the puncture needle are included in a three-dimensional scanning region, a maximum swing angle for swinging the ultrasound transducers is set, and a three-dimensional region defined by the maximum swing angle is scanned with ultrasonic waves. In other words, in order that both the puncture object and the puncture needle are included in a three-dimensional scanning region, the entire scanning region is scanned with ultrasonic waves.

In the 1D array prove having the swing mechanism as described above, a volume rate depends on the number of swings of the ultrasound transducer per unit time. In other words, the volume rate becomes higher as the number of swings per unit time increases, whereas the volume rate becomes lower as the number of swings decreases.

In order to observe a process of puncturing by the puncture needle with respect to the puncture object in the ablation treatment, it is required to track the position of the puncture needle in real time while acquiring and displaying an image in which the puncture object (lesion) is represented. For this, it is required to acquire and display a three-dimensional image or MPR image in which the puncture needle is represented in real time while acquiring and displaying a three-dimensional image or MPR image in which the puncture object is represented.

In the conventional art, the entire scanning region is scanned, so that it is possible to acquire and display an image in which a puncture object and a puncture needle are represented. However, the number of swings of the ultrasound transducer per unit time decreases, with the result that there is a problem that the volume rate becomes lower.

Consequently, it becomes difficult to acquire and display in real time a three-dimensional image or MPR image in which a puncture needle is represented, so that it is difficult to track the position of the puncture needle in real time.

SUMMARY OF THE INVENTION

The present invention has been devised to provide an ultrasound imaging apparatus capable of improving the real-time properties of the image representing a puncture needle while acquiring an image representing a puncture object and a method of generating ultrasound images.

In a first aspect of the present invention, an ultrasound imaging apparatus comprises: a scan part configured to scan a three-dimensional scanning region to acquire volume data in the scanning region; a controller configured to control the scan part to scan a three-dimensional first scanning region to acquire volume data in the first scanning region, and control the scan part to consecutively scan a second scanning region more than once to consecutively acquire volume data in the second scanning region, the second scanning region being smaller than the first scanning region and included in the first scanning region; an image generator configured to generate ultrasound image data in the first scanning region including the second scanning region based on the volume data in the first scanning region and, every time the volume data in the second scanning region is acquired by consecutively scanning more than once, update the volume data in the second scanning region to generate new ultrasound image data; and a display controller configured to control a display to display an ultrasound image based on the generated ultrasound image data and, every time the new ultrasound image data is generated, update the ultrasound image displayed on the display to control the display to display the ultrasound image.

According to the first aspect, the rate for updating the volume data in the second scanning region becomes faster by consecutively scanning the second scanning region more than once. Therefore, it becomes possible to improve the real-time properties of an ultrasound image in the second scanning region. Furthermore, it becomes possible to acquire the entire image of an imaging subject by scanning the first scanning region that is larger than the second scanning region. It becomes possible to improve the real-time properties of an ultrasound image representing a puncture needle while acquiring and displaying the ultrasound image representing a puncture object that is included in the first scanning region by including the puncture needle in the second scanning region.

Further, in a second aspect of the present invention, a method for generating an ultrasound image comprises: scanning a three-dimensional first scanning region with ultrasonic waves, and acquiring volume data in the first scanning region; consecutively scanning a second scanning region that is smaller than the first scanning region and that is included in the first scanning region with ultrasonic waves more than once, and consecutively acquiring volume data in the second scanning region; generating ultrasound image data in the first scanning region including the second scanning region based on the volume data in the first scanning region and, every time the volume data in the second scanning region is acquired by consecutive scan more than once, updating the volume data in the second scanning region and generating new ultrasound image data; and displaying an ultrasound image based on the generated ultrasound image data and, every time the new ultrasound image data is generated, updating the displayed ultrasound image and displaying.

BRIEF DESCRIPTION OF THE DRAWINGS

FIG. 1 is a block diagram showing an ultrasound imaging apparatus according to an embodiment of the present invention.

FIG. 2A is a schematic view showing the mechanism of an ultrasound probe installed in the ultrasound imaging apparatus according to the embodiment of the present invention.

FIG. 2B is a schematic view showing the mechanism of the ultrasound probe installed in the ultrasound imaging apparatus according to the embodiment of the present invention.

DETAILED DESCRIPTION OF THE EMBODIMENTS

Figure 3:
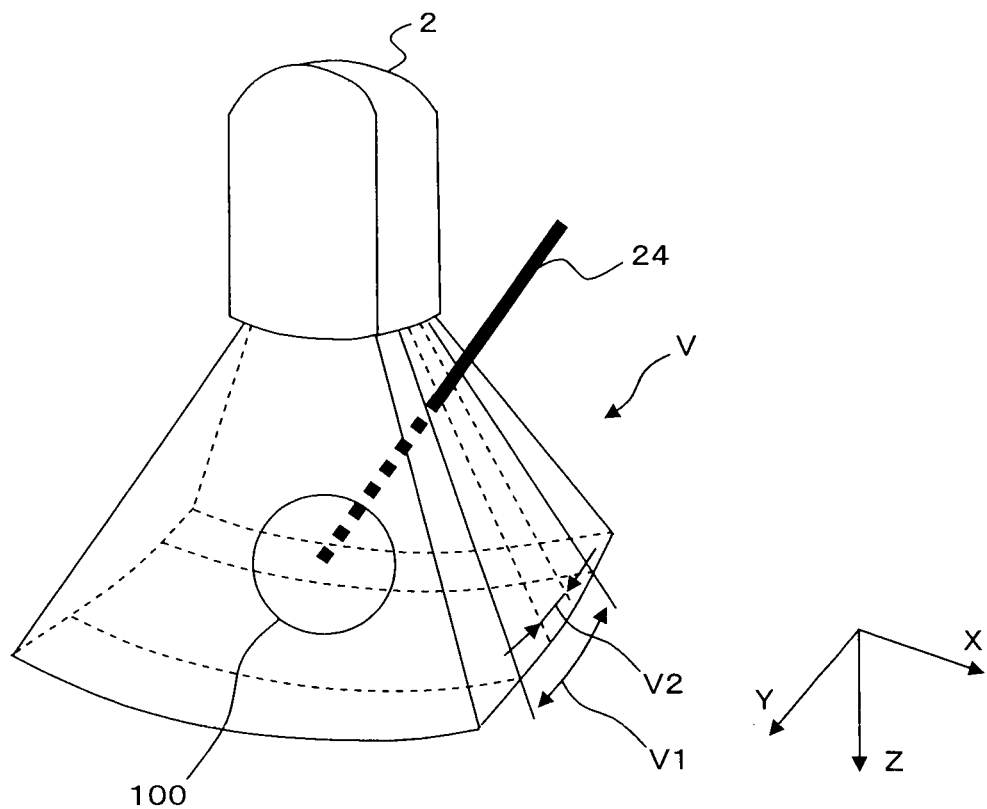
FIG. 3 is a conceptual view showing a three-dimensional scanning region scanned by the ultrasound imaging apparatus according to the embodiment of the present invention.

An ultrasound imaging apparatus according to an embodiment of the present invention will be described with reference to FIG. 1. FIG. 1 is a block diagram showing the ultrasound imaging apparatus according to the embodiment of the present invention.

An ultrasound imaging apparatus 1 according to the embodiment of the present invention includes an ultrasound probe 2, a transceiver 3, a signal processor 4, a storage 5, an image processor 6, a display controller 7, an user interface (UI) 8, and a controller 9.

As the ultrasound probe 2, a mechanical 1D array probe is used, which is a 1D array probe composed of a plurality of ultrasound transducers arranged in a row in a scanning direction and capable of scanning a three-dimensional region by mechanically swinging the plurality of the ultrasound transducers in a direction (swing direction) orthogonal to the scanning direction. Further, a 2D array probe composed of a plurality of ultrasound transducers arranged two-dimensionally may be used as the ultrasound probe 2. This embodiment describes a case in which the mechanical 1D array probe is used as the ultrasound probe 2 as an example.

Here, the ultrasound probe 2 of a mechanical 1D array probe will be described with reference to FIGS. 2A and 2B. FIGS. 2A and 2B are schematic views showing the mechanism of an ultrasound probe incorporated in the ultrasound imaging apparatus according to the embodiment of the present invention. FIG. 2A is a view of the ultrasound probe taken from a swing direction (Y direction). FIG. 2B is a view of the ultrasound probe taken from a scanning direction (X direction).

The ultrasound probe 2 of a mechanical 1D array probe scans a three-dimensional scanning region with ultrasonic waves by using both mechanical swing and electronic scan. The ultrasound probe 2 includes a group of ultrasound transducers 21, a swing mechanism 22, and a swing-angle detector 23. The group of ultrasound transducers 21 includes a plurality of ultrasound transducers arranged in a row in a scanning direction, which are not shown. As shown in FIG. 2A, a two-dimensional scan plane S along an arrangement direction of the ultrasound transducers (scanning direction) is electronically scanned with ultrasonic waves. Here, it is assumed that the arrangement direction of the group of ultrasound transducers 21 (scanning direction) is the X direction and a depth direction in which an ultrasonic beam is formed is a Z direction. The swing mechanism 22 is provided with a motor mechanism. As shown in FIG. 2B, the swing mechanism 22 swings the group of ultrasound transducers 21 by the motor mechanism in the Y direction (swing direction) orthogonal to the X direction and Z direction to mechanically scan. In FIG. 2B, the group of ultrasound transducers 21 with an angle thereof changed is shown by a dashed line. For example, the group of ultrasound transducers 21 is swung in the swing direction (Y direction) as shown in FIG. 2B while the scan plane S is electronically scanned with ultrasonic waves as shown in FIG. 2A, whereby a plurality of the scan planes S arranged in the swing direction are electronically scanned.

Thus, a three-dimensional scanning region V is scanned with ultrasonic waves. For example, the center position of swing is assumed to be 0 degree of the swing angle. The three-dimensional scanning region V is scanned with ultrasonic waves by reciprocating the group of ultrasound transducers 21 between a + direction and a − direction of the swing direction across the center position.

The swing-angle detector 23 includes an encoder that detects the amount of rotations of the motor of the swing mechanism 22 and detects an angle of the swing by the swing mechanism 22. The swing-angle detector 23 outputs swing angle information representing the detected swing angle to a swing controller 91. The swing controller 91 controls the operation of the motor of the swing mechanism 22 in accordance with the swing angle information.

The swing controller 91 drives the swing mechanism 22 incorporated in the ultrasound probe 2 in accordance with a swing condition stored in an operation-condition storage 93. Thus, the group of ultrasound transducers 21 incorporated in the ultrasound probe 2 is swung, which allows the mechanical scan. At this moment, the swing controller 91 controls the group of ultrasound transducers 21 to swing at a predetermined swing speed within a range of a predetermined swing angle, in accordance with the swing condition including swing angle information representing a swing angle and swing speed information representing a swing speed. The swing speed is a speed for causing the group of ultrasound transducers 21 to swing in the swing direction (Y direction).

The operator can input the swing angle information and the swing speed information by using an operation part 82. The swing angle information and the swing speed information inputted through the operation part 82 are outputted to the controller 9 from the user interface (UI) 8, and stored as the swing condition into the operation-condition storage 93 of the controller 9.

The transceiver 3 includes a transmitter and a receiver. The transceiver 3 supplies an electric signal to the ultrasound probe 2 so as to generate ultrasonic waves, and receives an echo signal received by the ultrasound probe 2. The transceiver 3 performs scan (electronic scan) of the scan plane S defined by an angle in the scanning direction (X direction) shown in FIG. 2A by using the ultrasound probe 2. At this moment, in accordance with electronic scan conditions including information representing an angle in the scanning direction (X direction), the density of scanning lines, etc., the controller 9 controls the electronic scan of the transceiver 3 so that the scan plane S is electronically scanned.

The operator can input the electronic scan conditions such as the density of scanning lines by using the operation part 82. The electronic scan conditions inputted through the operation part 82 are outputted to the controller 9 from the user interface (UI) 8, and stored into the operation-condition storage 93 of the controller 9.

The transmitter of the transceiver 3 is provided with a clock generation circuit, a transmission delay circuit, and a pulsar circuit, which are not shown. The clock generation circuit generates clock signals that determine the transmission timing and transmission frequency of ultrasound signals. The transmission delay circuit applies delay at the time of transmission of ultrasonic waves to execute transmission focus. The pulsar circuit has a corresponding number of pulsars to that of individual channels corresponding to the respective ultrasound transducers. The pulsar circuit generates a driving pulse at the delayed transmission timing, and supplies oscillation energy to the respective ultrasound transducers of the ultrasound probe 2.

The receiver of the transceiver 3 is provided with a preamplifier circuit, an A/D conversion circuit, a reception delay circuit, and an adder circuit, which are not shown. The preamplifier circuit amplifies echo signals outputted from the respective ultrasound transducers of the ultrasound probe 2 for each reception channel. The A/D conversion circuit executes A/D conversion on the amplified echo signals. The reception delay circuit applies a delay time necessary for determining the reception directionality of the echo signals after the A/D conversion.

The adder circuit adds echo signals to which the delay time is applied.

As a result of the addition, a reflection component from a direction according to the reception directionality is magnified. The signals to after the adding process by the transceiver 3 may be referred to as "RF signals." The RF signals outputted from the transceiver 3 are outputted to the signal processor 4.

The signal processor 4 is provided with a B-mode processor. The B-mode processor visually images amplitude information of the echoes, thereby generating B-mode ultrasound raster data from the echo signals.

More specifically, the B-mode processor executes a band pass filter process on the signals sent from the transceiver 3, and then detects the envelope curve of the output signals. The B-mode processor then visually images the amplitude information of the echoes by executing a compression process by logarithmic transformation on the detected data.

Moreover, the signal processor 4 may be provided with a Doppler processor. The Doppler processor, for example, executes quadrature detection of the received signals sent from the transceiver 3 to extract Doppler shift frequency components, and further executes an FFT processing to generate a Doppler frequency distribution representing a blood flow velocity.

Signals outputted from the transceiver 3 are subjected to a predetermined process at any of the processors. The signal processor 4 outputs ultrasound raster data to the storage 5.

A storage 5 is composed of a storing device such as memory and a hard disk drive. The storage 5 stores ultrasonic raster data generated by the signal processor 4. In this embodiment, a three-dimensional scanning region is scanned by performing mechanical scan and electronic scan. As a result, volume data configured by a plurality of scan planes is acquired and stored into the storage 5.

In this embodiment, the group of ultrasound transducers 21 is swung so that a puncture object (lesion) subjected to ablation treatment with a puncture needle and the puncture needle are included in a three-dimensional scanning region to be scanned with ultrasonic waves.

Three-dimensional scanning regions scanned with ultrasonic waves and a sequence for scanning the scanning regions will be described with reference to FIGS. 3 and 4. FIG. 3 is a conceptual view showing three-dimensional scanning regions scanned by the ultrasound imaging apparatus according to the embodiment of the present invention.

Figure 4:
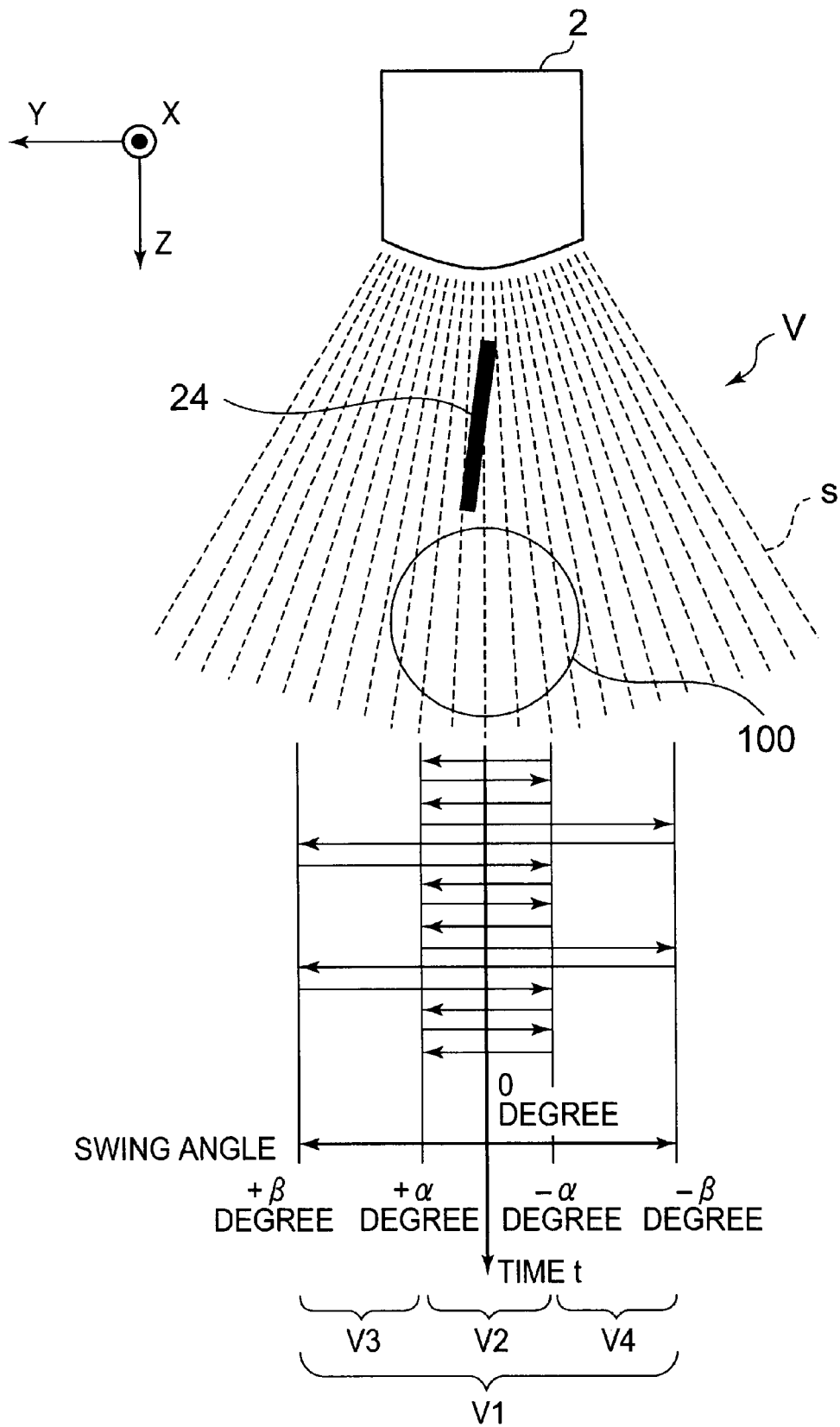
FIG. 4 is a conceptual view showing a three-dimensional operation region scanned by the ultrasound imaging apparatus according to the embodiment of the present invention, and showing a sequence for scanning the scanning region.

FIG. 4 is a conceptual view showing three-dimensional scanning regions scanned by the ultrasound imaging apparatus according to the embodiment of the present invention and the sequence for scanning the scanning regions.

As shown in FIG. 3, a three-dimensional scanning region V is scanned by performing electronic scan in the X direction while swinging the group of ultrasound transducers 21 of the ultrasound probe 2 in the swing direction (Y direction). In this embodiment, a three-dimensional first scanning region V1 having a predetermined size is scanned with ultrasonic waves, and furthermore, scans a three-dimensional second scanning region V2 that is smaller than the first scanning region V1 and is included in the first scanning region V1 with ultrasonic waves. For imaging a puncture object (lesion) and a puncture needle, a puncture object 100 is included in the first scanning region V1 and a puncture needle 24 is included in the second scanning region V2. In other words, the first scanning region V1 is set so as to include the puncture object 100 and the second scanning region V2 is set so as to include the puncture needle 24.

The first scanning region V1 and the second scanning region V2 are each designated by a swing angle. For example, as shown in FIG. 4, the center position of swing is set to 0 degree of a swing angle. A range from +α degree to −α degree of swing angle is assumed to be the second scanning region V2. A range from +β degree to −β degree of swing angle is assumed to be the first scanning region V1. Because the absolute value of the +β degree and −β degree is greater than the absolute value of +α degree and −α degree, the second scanning region V2 is included in the first scanning region V1. In other words, since the range from +α degree to −α degree is included between +β degree and −β degree, so the second scanning region V2 is included in the first scanning region V1.

In this embodiment, a range that is substantially in the center in the swing direction (Y direction) within the first scanning region V1 is set to the range of the second scanning region V2. Further, regions other than the first scanning region V1 are also defined by swing angles. For example, the range of a swing angle from +α degree to +β degree is set as a third scanning region V3, and the range of a swing angle from −α degree to −β degree is set to a fourth scanning region V4. A range from +α degree to −α degree of the swing angle, and is equivalent to an example of the "range of the second swing angle" and the range from +β degree to −β degree of the swing angle is equivalent to an example of the "range of the first swing angle" in the present invention.

The operator can use the operation part 82 to input swing angle information for defining the first scanning region V1 (+β degree and −β degree) and input swing angle information for defining the second scanning region V2 (+α degree and −α degree). For example, the operator uses the operation part 82 to input ±30 degrees as the swing angle information for defining the first scanning region V1 (±β degrees) and inputs ±10 degrees as the swing angle information for defining the second scanning region V2 (±α degrees). The swing angle information (±α degrees and ±β degrees) inputted through the operation part 82 is outputted from the user interface (UI) 8 to the controller 9, and is stored in the operation-condition storage 93 of the controller 9 as swing the conditions. Furthermore, the operator uses the operation part 82 to input the swing speed information indicating the swing speed in the first scanning region V1 and the swing speed information indicating the swing speed in the second scanning region V2. The swing speed in the first scanning region V1 and the swing speed in the second scanning region V2 may be the same speed, or may be different speeds.

The transceiver 3 causes the group of ultrasound transducers 21 to generate an ultrasonic beam, and the scan plane S is scanned by electronically scanning with the ultrasonic beam in the scanning direction (X direction). The swing mechanism 22 mechanically swings the group of ultrasound transducers 21 from −α degree to +α degree in the swing direction (Y direction) under the control of the swing controller 91 while the electronic scan is executed, whereby the three-dimensional second scanning region V2 is scanned with the ultrasonic beam. As a result, volume data in the second scanning region V2 is acquired. Furthermore, the swing mechanism 22 mechanically swings the group of ultrasound transducers 21 from +α degree to −α degree in the swing direction (Y direction) under the control of the swing controller 91, whereby the second scanning region V2 is scanned with the ultrasonic beam. As a result, volume data in the second scanning region V2 is acquired. In other words, by swinging the group of ultrasound transducers 21 in the second scanning region V2 so as to reciprocate, it is possible to acquire two volume data in the second scanning region V2.

Likewise, the transceiver 3 electronically scans with an ultrasonic beam in the scanning direction (X direction) to scan the scan plane S. The swing mechanism 22 mechanically swings the group of ultrasound transducers 21 from −β degree to +β degree in the swing direction (Y direction) under the control of the swing controller 91 while the electronic scan is executed, whereby the three-dimensional first scanning region V1 is scanned with the ultrasonic beam. As a result, volume data in the first scanning region V1 is acquired. The first scanning region V1 includes the second scanning region V2, the third scanning region V3, and a fourth scanning region V4. Therefore, the volume data in the first scanning region V1 includes the volume data in the second scanning region V2, the volume data in the third scanning region V3, and the volume data in the fourth scanning region V4. In other words, by swinging the group of ultrasound transducers 21 from −β degree to +β degree in the swing direction (Y direction), the fourth scanning region V4, the second scanning region V2, and third scanning region V3 are sequentially scanned with the ultrasonic beam.

Consequently, the volume data in the fourth scanning region V4, the volume data in the second scanning region V2, and the volume data in the third scanning region V3 are sequentially acquired. Furthermore, the swing mechanism 22 mechanically swings the group of ultrasound transducers 21 from +β degree to −β degree in the swing direction (Y direction) under the control of the swing controller 91, whereby the first scanning region V1 is scanned with the ultrasonic beam. As a result, volume data in the first scanning region V1 is acquired. In other words, by swinging the group of ultrasound transducers 21 in a reciprocating manner in the first scanning region V1, two volume data in the first scanning region V1 are acquired.

Furthermore, the transceiver 3 electronically scans with an ultrasonic beam in the scanning direction (X direction) to scan the scan plane S. The swing mechanism 22 mechanically swings the group of ultrasound transducers 21 from +α degree to −β degree in the swing direction (Y direction) under the control of the swing controller 91 while the electronic scan is executed, the second scanning region V2 and the fourth scanning region V4 are sequentially scanned with the ultrasonic beam. As a result, volume data in the second scanning region V2 and volume data in the fourth scanning region V4 are sequentially acquired. Moreover, the swing mechanism 22 mechanically swings the group of ultrasound transducers 21 from +β degree to −α degree in the swing direction (Y direction) under the control of the swing controller 91, the third scanning region V3 and the second scanning region V2 are sequentially scanned with the ultrasonic beam. As a result, volume data in the third scanning region V3 and volume data in the second scanning region V2 are sequentially acquired.

In this embodiment, the swing controller 91 controls the group of ultrasound transducers 21 to consecutively swing more than once in the second scanning region V2 in which the subject is a puncture needle, and the transceiver 3 consecutively scans the second scanning region V2 more than once. Consequently, the transceiver 3 consecutively acquires the volume data in the second scanning region V2 more than once.

In this embodiment, in a swing of the group of ultrasound transducers 21, a scan from the return of the swing to the other return is counted as a single scan. For example, a scan of a range from −α degree to +α degree is counted as a single scan. Likewise, a scan of a range from +α degree to −α degree is counted as a single scan. The swing controller 91 counts the number of return swings and the group of ultrasound transducers 21 is consecutively swung more than once in the second scanning region V2.

For example, the swing controller 91 controls the group of ultrasound transducers 21 to consecutively swing more than once in the second scanning region V2, and thereafter, swings the group of ultrasound transducers 21 is swung once in the first scanning region V1.

In other words, the swing controller 91 controls the group of ultrasound transducers 21 to consecutively swing more than once in the second scanning region V2 every time the group of ultrasound transducers 21 is swung once in the first scanning region V1. To be specific, the swing controller 91 controls the group of ultrasound transducers 21 to consecutively swing more than once in the second scanning region V2 while counting the number of returns of the swings, thereafter, controls the group of ultrasound transducers 21 to swing once in the first scanning region V1, and thereafter controls the group of ultrasound transducers 21 to consecutively swing more than once in the second scanning region V2. Thereafter, the swing controller 91 repeatedly executes the scan of the first scanning region V1 and the scan of the second scanning region V2 while alternately switching the scans.

Thus, the transceiver 3 consecutively acquires volume data in the second scanning region V2 more than once and further acquires volume data in the first scanning region V1. In other words, the transceiver 3 acquires the volume data in the fourth scanning region V4, the volume data in the second scanning region V2, and the volume data in the third scanning region V3, while consecutively scanning more than once.

The operator can use the operation part 82 to input the number of times for consecutively scanning the second scanning region V2.

Number-of-times information representing the number of inputs from the operation part 82 is outputted from the user interface (UI) 8 to the controller 9, and stored in the operation-condition storage 93 of the controller 9. The swing controller 91 controls the swing operation of the swing mechanism 22 in accordance with the number-of-times information included in the swing conditions, thereby consecutively swinging the group of ultrasound transducers 21 more than once in the second scanning region V2.

As described above, the swing conditions according to the embodiment include the swing-angle information, the swing-speed information and the number-of-times information, and are stored in the operation-condition storage 93.

The image generator 6 is provided with a data acquiring part 61 and an image generator 62. The data acquiring part 61 acquires volume data in each scanning region from the storage 5 and outputs to the image generator 62 under the control of an image generation controller 92. The image generation controller 92 outputs, to the data acquiring part 61, swing angle information representing the swing angle included in the swing conditions and time information representing the duration of time of scan of each scanning region defined by the swing angle. The duration of time of scan of each scanning region is obtained from the swing angle and the swing speed with reference to the time of start of scan. For example, the controller 9 obtains the duration of time of scan of each scanning region, based on the swing angle and the swing speed.

In accordance with the swing angle information and time information outputted from the image generation controller 92, the data acquiring part 61 acquires, from the storage 5, volume data in each scanning region defined by the swing angle, which is volume data acquired at the closest time, and outputs the volume data to the image generator 62.

For example, in a case where volume data in the second scanning region V2 is acquired, the data acquiring part 61 acquires volume data in the second scanning region V2 acquired at the closest time, from the storage 5 in accordance with the swing angle information and time information representing the range of the second scanning region V2 outputted from the image generation controller 92, and outputs the volume data to the image generator 62. Further, in a case where volume data in the third scanning region V3 is acquired, the data acquiring part 61 acquires volume data in the third scanning region V3 acquired at the closest time, from the storage 5 in accordance with the swing angle information and time information representing the range of the third scanning region V3, and outputs the volume data to the image generator 62. Further, in a case where volume data in the fourth scanning region V4 is acquired, the data acquiring part 61 acquires volume data in the fourth scanning region V4 acquired at the closest time, from the storage 5 in accordance with the swing angle information and time information representing the range of the fourth scanning region V4, and outputs the volume data to the image generator 62.

The image generator 62 executes volume rendering on volume data composed of data from a plurality of scan planes, thereby generating three-dimensional image data representing the morphology of tissues of the subject. Further, the image generator 62 may execute the MPR (multi planar reconstruction) process on the volume data, thereby generating image data (MPR image data) at an arbitrary cross-section. Moreover, the image generator 62 may execute the MIP (maximum intensity projection) process on the volume data, thereby generating maximum-value projection image data (MIP image data). The image generator 62 outputs ultrasound image data such as three-dimensional image data and MPR image data to the display controller 7. The display controller 7 controls the display 81 to display a three-dimensional image based on the three-dimensional image data or an MPR image based on the MPR image data.

Furthermore, the image generator 62 may execute the digital scan conversion process on ultrasound raster data from each scan plane, thereby generating isotropic voxel data or anisotropic voxel data.

Further, the image generator 62 may execute the volume rendering or MPR process on the voxel data, thereby generating three-dimensional image data or MPR image data.

In this embodiment, the image generator 62 combines volume data of the respective scanning regions acquired by the data acquiring part 61. The image generator 62 executes the volume rendering or MPR process on the combined single volume data, thereby generating three-dimensional image data or MPR image data. The display controller 7 controls the display 81 to display a three-dimensional image or an MPR image based on the combined volume data.

For example, when volume data of the second scanning region V2 is acquired by the transceiver 3 and the volume data is outputted from the data acquiring part 61 to the image generator 62, the image generator 62 generates three-dimensional image data or MPR image data based on the volume data. The display controller 7 controls the display 81 to display a three-dimensional image or an MPR image of the second scanning region V2. Consequently, a tissue and a puncture needle included in the second scanning region V2 are shown in the three-dimensional image. Furthermore, morphologies at a cross-section of the tissue and the puncture needle included in the second scanning region V2 are shown in the MPR image.

Furthermore, when volume data of the third scanning region V3 is acquired by the transceiver 3 and the volume data of the second scanning region V2 and the volume data of the third scanning region V3 are outputted from the data acquiring part 61 to the image generator 62, the image generator 62 combines the two volume data. The image generator 62 generates three-dimensional image data or MPR image data based on the combined volume data. The display controller 7 controls the display 81 to display three-dimensional images or MPR images of the second scanning region V2 and the third scanning region V3.

Consequently, tissues and puncture needles included in the second scanning region V2 and the third scanning region V3 are represented in three-dimensional image. Furthermore, the morphologies at cross-sections of the tissues and the puncture needles included in the second scanning region V2 and the third scanning region V3 are shown in the MPR image.

When volume data of the respective scanning regions are sequentially acquired by the transceiver 3, the data acquiring part 61 acquires volume data of the respective scanning regions, which are volume data acquired at the closest time, from the storage 5, and outputs the volume data to the image generator 62. The image generator 62 updates the volume data of the respective scanning regions to volume data acquired at the closest time, thereby generating three-dimensional image data or MPR image data at the closest time. The display controller 7 controls the display 81 to display the updated three-dimensional image or MPR image. Consequently, the three-dimensional image or the MPR image in each scanning region is updated and displayed on the display 81.

In this embodiment, in the second scanning region V2 where a puncture needle is the target, the group of ultrasound transducers 21 is consecutively swung more than once, whereby the transceiver 3 consecutively scans the second scanning region V2 more than once.

Consequently, the transceiver 3 consecutively obtains the volume data in the second scanning region V2. The image generator 62 consecutively generates three-dimensional image data or MPR image data more than once in the second scanning region V2. Then, the display controller 7 controls the display 81 to display a three-dimensional image or an MPR image, which is an updated image of the second scanning region V2.

Thus, the second scanning region V2 is consecutively scanned more than once every time the first scanning region V1 is scanned once, whereby the timing for updating the volume data in the second scanning region V2 becomes faster. Therefore, a three-dimensional image or an MPR image showing a puncture needle becomes more real-time.

Furthermore, by scanning the first scanning region V1, it is possible to acquire and display a three-dimensional image or an MPR image representing the entire image of a puncture object (lesion). As described above, according to the ultrasound imaging apparatus according to this embodiment, it becomes possible to make a three-dimensional image or an MPR image representing a puncture needle more real-time while acquiring and displaying a three-dimensional image or an MPR image representing the entire image of a puncture object (lesion).

Consequently, it becomes possible to observe a puncturing process for a puncture object by tracking the position of a puncture needle in real time while checking the entire image of the puncture object (lesion).

In a case where a scan plane is scanned with ultrasonic waves without swinging the group of ultrasound transducers 21, the image generator 62 may generate ultrasound image data at the scan plane. For example, the image generator 62 is provided with a DSC (digital scan converter) and, in order to obtain an image represented by an orthogonal coordinate system, may convert data processed by the signal processor 4 into image data represented by an orthogonal coordinate system (scan conversion process). As an example, the image generator 62 generates cross-section image data as two-dimensional information based on B-mode ultrasound raster data, and the display controller 7 controls the display 81 to display a cross-section image based on the cross-section image data.

The controller 9 is provided with the swing controller 91, the image generation controller 92, and the operation-condition storage 93.

As described above, the swing controller 91 controls a swing operation by the swing mechanism 22 of the ultrasound probe 2.

Moreover, the image generation controller 92 controls data acquisition by the data acquiring part 61 of the image processor 6.

Furthermore, the operation-condition storage 93 stores swing conditions including the swing angle, the swing speed and the number-of-times information and conditions such as the density of scanning lines of an ultrasonic beam. Furthermore, the controller 9 controls transmission and reception of ultrasonic waves by the transceiver 3.

The user interface (UI) 8 is provided with the display 81 and the operation part 82. The display 81 is composed of a monitor such as a CRT and a liquid crystal display, and displays a three-dimensional image or an MPR image. The operation part 82 receives input of conditions such as the swing angle, the swing speed, or the density of the scanning lines. The operation part 82 is composed of a pointing device such as a joystick and a trackball, a switch, various buttons, a keyboard, a mouse, a TCS (touch command screen), or the like.

The image processor 6, the display controller 7 and the controller 9 are composed of a CPU (central processing unit) and a storing device such as a ROM (read only memory) and a RAM (random access memory). The storing device stores an image-processing program for executing the function of the image processor 6, a display-controlling program for executing the function of the display controller 7, and a control program for executing the function of the controller 9. The image-processing program includes a data acquisition program for executing the function of the data acquiring part 61, and an image-generating program for executing the function of the image generator 62. Furthermore, the control program includes a swing control program for executing the function of the swing controller 91, and an image generation control program for executing the function of the image generation controller 92. The CPU executes the data acquisition program to acquire volume data in each scanning region from the storage 5. Further, the CPU executes the image-generating program to execute image processing such as volume rendering on the volume data.

Moreover, the CPU executes the display control program to control the display 81 to display an image such as a three-dimensional image. Furthermore, the CPU executes the swing control program to control the operation of the swing mechanism 22 of the ultrasound probe 2. Moreover, the CPU executes the image generation control program to control data reading by the data acquiring part 61.

Next, an example of the swing operation of the group of ultrasound transducers 21 will be described.

(First Operation Example)

Figure 5:
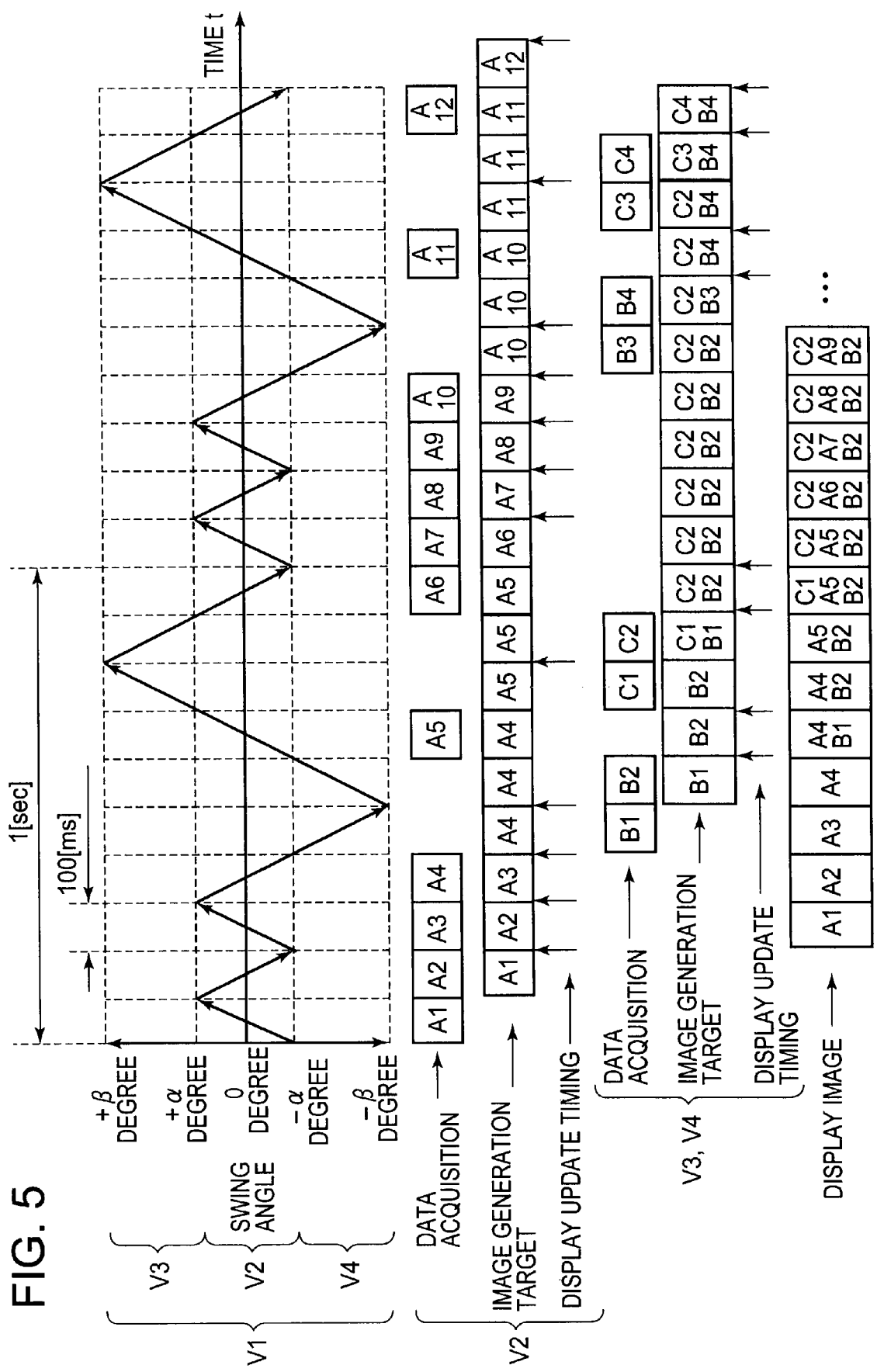
FIG. 5 is a conceptual view for explaining a first operation example of the ultrasound imaging apparatus according to the embodiment of the present invention.

First, a first operation example will be described with reference to FIG. 5. FIG. 5 is a conceptual view for explaining the first operation example according to the ultrasound imaging apparatus according to the embodiment of the present invention. In a graph shown in FIG. 5, the horizontal axis takes time t, and the vertical axis takes a swing angle. In FIG. 5, timing of data acquisition in each scanning region, data subjected to image generation, and timing for updating the display are shown.

In the first operation example, scan is performed in a state where a swing speed for swinging the group of ultrasound transducers 21 is kept constant and the widths of the range of the swing angle in the second scanning region V2 (range from $-\alpha$ degree to $+\alpha$ degree), the range of the swing angle in the third scanning region V3 (range from $+\alpha$ degree to $+\beta$ degree) and the range of the swing angle in the fourth scanning region V4 (range from $-\alpha$ degree to $-\beta$ degree) are set to be equal. In other words, the widths in the swing direction (Y direction) of the respective scanning regions are set to be equal to perform scan for the second scanning region V2, the third scanning region V3 and the fourth scanning region V4.

Furthermore, in this embodiment, as an example, a case of consecutively scanning the second scanning region V2 four times every time the first scanning region V1 is scanned once. Thus, the swing controller 91 controls to consecutively swing the group of ultrasound transducers 21 four times in the second scanning region V2 while counting the return of the swing.

First, under the control of the controller 9, the transceiver 3 causes the group of ultrasound transducers 21 to generate an ultrasonic beam, and the scan plane S is scanned by electronic scan with the ultrasonic beam in the scanning direction (X direction). While the electronic scan is performed, the swing mechanism 22 mechanically swings the group of ultrasound transducers 21 from $-\alpha$ degree to $+\alpha$ degree in the swing direction (Y direction) under the control of the swing controller 91. Consequently, the transceiver 3 acquires volume data A1 of the second scanning region V2, and the volume data A1 is stored in the storage 5.

Under the control of the image generation controller 92, the data acquiring part 61 acquires the volume data A1 of the second scanning region V2 acquired at the closest time, from the storage 5, and outputs the volume data to the image generator 62. The image generator 62 generates three-dimensional image data or MPR image data based on the volume data A1, and the display controller 7 causes the display 81 to display a three-dimensional image or an MPR image. Thus, the three dimensional shapes of a tissue and a puncture needle included in the second scanning region V2, and the shape thereof at a cross-section are represented.

On the other hand, the swing-angle detector 23 detects a swing angle. The swing controller 91 gives the swing mechanism 22 an instruction to return when the detected swing angle reaches $+\alpha$ degree.

In response to the instruction from the swing controller 91, the swing mechanism 22 mechanically swings the group of ultrasound transducers 21 from $+\alpha$ degree to $-\alpha$ degree. Thus, the transceiver 3 acquires volume data A2 of the second scanning region V2, and the volume data A2 is stored in the storage 5. Then, under the control of the image generation controller 92, the data acquiring part 61 acquires the volume data A2 of the second scanning region V2 acquired at the closest time, from the storage 5, and outputs the volume data to the image generator 62. The image generator 62 generates three-dimensional image data or MPR image data based on the volume data A2. The display controller 7 causes the display 81 to display a new three-dimensional image or an MPR image by updating the image displayed on the display 81. Consequently, the three-dimensional image or the MPR image of the second scanning region V2 in which a puncture needle is included is updated and displayed on the display 81.

Subsequently, in response to the instruction from the swing controller 91, the swing mechanism 22 causes the group of ultrasound transducers 21 to mechanically swing from $-\alpha$ degree to $+\alpha$ degree and further mechanically swings the group of ultrasound transducers 21 from $+\alpha$ degree to $-\alpha$ degree. Thus, the transceiver 3 sequentially acquires volume data A3 and A4 in the second scanning region V2. The data acquiring part 61 sequentially acquires the volume data A3 and A4 from the storage 5 and outputs the volume data to the image generator 62. The image generator 62 sequentially generates three-dimensional image data or MPR image data based on the volume data A3 and A4, respectively. The display controller 7 updates the image displayed on the display 81 and causes the display 81 to display a new three-dimensional image or an MPR image. Thereby, a three-dimensional image or an MPR image in the second scanning region V2 in which a puncture needle is included is updated and displayed on the display 81.

In the example shown in FIG. 5, after consecutively swinging the group of ultrasound transducers 21 four times in the second scanning region V2, the swing controller 91 swings the group of ultrasound transducers 21 from $-\alpha$ degree to $-\beta$ degree. In other words, the swing controller 91 counts the number of returns of swings in the second scanning region V2 and, when the number reaches four, swings the group of ultrasound transducers 21 from $-\alpha$ degree to $-\beta$ degree. Thus, the transceiver 3 acquires volume data B1 in the fourth scanning region V4. Receiving the swing angle information and the time information from the image generation controller 92, the data acquiring part 61 acquires volume data of the respective scanning regions acquired at the closest time, from the storage 5, and outputs the volume data to the image processor 6.

For example, the data acquiring part 61 acquires the volume data A4 from the storage 5 and outputs the volume data to the image generator 62 with regard to the second scanning region V2, and acquires the volume data B1 from the storage 5 and outputs the volume data to the image generator 62 with regard to the fourth scanning region V4.

Then, the image generator 62 combines the volume data A4 and the volume data B1, and generates three-dimensional image data or MPR image data based on the combined volume data. The display controller 7 updates an image displayed on the display 81 and causes the display 81 to display a three-dimensional image or an MPR image in which the second scanning region V2 and the fourth scanning region V4 are represented.

Then, the swing controller 91 controls the group of ultrasound transducers 21 to swing from $-\beta$ degree to $+\beta$ degree. Consequently, the transceiver 3 sequentially scans the fourth scanning region V4, the second scanning region V2, and the third scanning region V3. As a result, the transceiver 3 sequentially acquires volume data B2 in the fourth scanning region V4, volume data A5 in the second scanning region V2, and volume data C1 in the third scanning region V3.

Under the control of the image generation controller 92, the data acquiring part 61 acquires the volume data A4 from the storage 5 and outputs the volume data to the image generator 62 with regard to the second scanning region V2, and acquires the volume data B2 from the storage 5 and outputs the volume data to the image generator 62 with regard to the fourth scanning region V4. The image generator 62 combines the volume data A4 and volume data B2, and generates three-dimensional image data or MPR image data based on the combined volume data. In other words, for the fourth scanning region V4, the image generator 62 uses the volume data B2 acquired at the closest time instead of the volume data B1, and combines the volume data B2 and the volume data A4. The display controller 7 updates the image displayed on the display 81 and causes the display 81 to display a new three-dimensional image or MPR image. Thus, the three-dimensional image or the MPR image in the fourth scanning region V4 is updated and displayed on the display 81.

After that, the data acquiring part 61 acquires volume data A5 acquired at the closest time from the storage 5 with regard to the second scanning region V2 and acquires the volume data B2 from the storage 5 with regard to the fourth scanning region V4, and outputs the volume data to the image generator 62. The image generator 62 combines the volume data A5 and the volume data B2, and generates three-dimensional image data or MPR image data based on the combined volume data. In other words, the image generator 62 uses the volume data A5 acquired at the closest time instead of the volume data A4 with regard to the second scanning region V2, and combines the volume data A5 with the volume data B2. The display controller 7 updates the image displayed on the display 81 and causes the display 81 to display a new three-dimensional image or MPR image. Thus, the three-dimensional image or the MPR image in the second scanning region V2 in which a puncture needle is included is updated and displayed on the display 81.

After that, the data acquiring part 61 acquires the volume data A5 from the storage 5 with regard to the second scanning region V2, acquires the volume data B2 from the storage 5 with regard to the fourth scanning region V4, and acquires the volume data C1 acquired at the closest time from the storage 5 with regard to the third scanning region V3, and outputs the volume data to the image generator 62. The image generator 62 combines the volume data A5, the volume data B2 and the volume data C1, and generates three-dimensional image data or MPR image data based on the combined volume data. The display controller 7 updates the image displayed on the display 81 and causes the display 81 to display a three-dimensional image or an MPR image in which the second scanning region V2, the third scanning region V3 and the fourth scanning region V4 are represented. Thus, a three-dimensional image or an MPR image representing the entire scanning region V1 is displayed on the display 81. In other words, a three-dimensional image or an MPR image representing the entire image of the puncture object (lesion) is displayed on the display 81.

Then, the swing controller 91 causes the group of ultrasound transducers 21 to swing from +β degree to −α degree. Consequently, the transceiver 3 sequentially scans the third scanning region V3 and the second scanning region V2. As a result, the transceiver 3 sequentially acquires volume data C2 in the third scanning region V3 and volume data A6 in the second scanning region V2.

Under the control of the image generation controller 92, the data acquiring part 61 acquires the volume data A5 from the storage 5 and outputs the volume data to the image generator 62 with regard to the second scanning region V2, acquires the volume data B2 from the storage 5 and outputs the volume data to the image generator 62 with regard to the fourth scanning region V4, and acquires the volume data C2 acquired at the closest time from the storage 5 and outputs the volume data to the image generator 62 with regard to the third scanning region V3. The image generator 62 combines the volume data A5, the volume data B2 and the volume data C2, and generates three-dimensional image data or MPR image data based on the combined volume data. In other words, the image generator 62 uses the volume data C2 acquired at the closest time instead of the volume data C1 with regard to the third scanning region V3, and combines the volume data C2, the volume data B2 and the volume data A5. The display controller 7 updates the image displayed on the display 81 and causes the display 81 to display a new three-dimensional image or MPR image. Thus, the three-dimensional image or the MPR image in the third scanning region V3 is updated and displayed on the display 81.

Thereafter, the data acquiring part 61 acquires the volume data A6 acquired at the closest time from the storage 5 with regard to the second scanning region V2, acquires the volume data B2 from the storage 5 with regard to the fourth scanning region V4, and acquires the volume data C2 from the storage 5 with regard to the third scanning region V3, and outputs the volume data to the image generator 62. The image generator 62 combines the volume data A6, volume data B2, and volume data C2 to generate three-dimensional image data or MPR image data based on the combined volume data. In other words, the image generator 62 uses the volume data A6 acquired at the closest time instead of the volume data A5 with regard to the second scanning region V2, and combines the volume data A6, volume data B2, and volume data C2. The display controller 7 updates the image displayed on the display 81 and causes the display 81 to display a new three-dimensional image or MPR image. Thus, the three-dimensional image or the MPR image in the second scanning region V2 in which a puncture needle is included is updated and displayed on the display 81.

After that, the swing controller 91 repeatedly executes the above swing sequence, whereby the swing mechanism 22 causes the group of ultrasound transducers 21 to consecutively swing more than once in the second scanning region V2.

In the example shown in FIG. 5, the second scanning region V2 including the puncture needle is scanned six times per second, and the first scanning region V1 is scanned 1.5 times. Specifically, within one second, the volume data A1 through A6 in the second scanning region V2 are acquired, the volume data B1 and B2 in the fourth scanning region V4 are acquired, and the volume data C1 and C2 in the third scanning region V3 are acquired.

In the example shown in FIG. 5, it takes 100 ms to scan each of the scanning regions in one scan. Specifically, it takes 100 ms to scan the second scanning region V2. It also takes 100 ms to scan each of the third and fourth scanning regions V3 and V4. Moreover, when a time to scan a single scan plane S is 25 ms, scan of four scan planes S is regarded as scan of a single scanning region.

Although it takes the same amount of time (100 ms) to scan each of the second, third and fourth scanning regions V2, V3 and V4, the duration for scanning each of the scanning regions may be changed. For example, when the swing speed is kept constant, the duration for scanning each of the scanning regions may be changed by changing the size of the range of each of the scanning regions. Further, by changing the duration for scanning a single scan plane S in each of the scanning regions, the duration for scanning each of the scanning regions may be changed. Moreover, the number of the scan planes S in each of the scanning regions may be changed.

(Comparison with Conventional Art)

Figure 10:
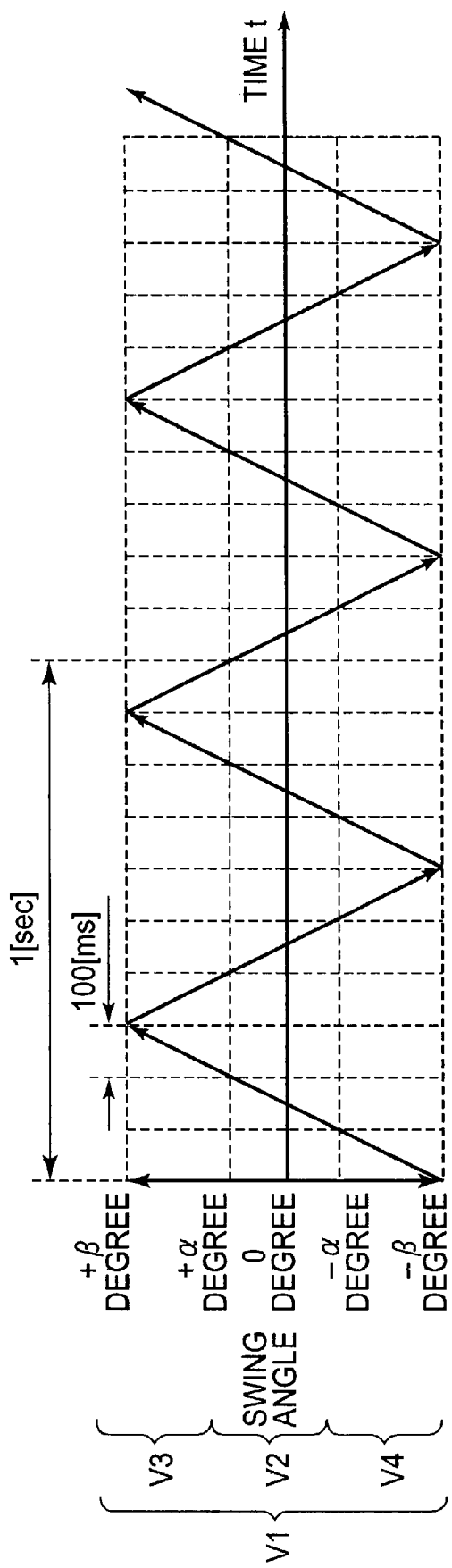
FIG. 10 is a conceptual view for explaining a swing operation in the conventional art.

Here, the swing operation by the ultrasound imaging apparatus 1 according to this embodiment and the swing operation according to the conventional art will be compared with reference to FIG. 5 and FIG. 10.

FIG. 10 is a conceptual view for explaining the swing operation in the conventional art. In a graph shown in FIG. 10, the horizontal axis takes time t, and the vertical axis takes a swing angle.

As shown in FIG. 10, in the conventional art, a group of ultrasound transducers is mechanically swung in a swing direction (Y direction) from −β degree to +β degree and then swung from +β degree to −β degree, and this swing is repeatedly performed. When a swing speed in the conventional art is equal to the swing speed in this embodiment, the second scanning region V2 is scanned three times in one second and three volume data are acquired in the swing operation in the conventional art. On the other hand, according to the ultrasound imaging apparatus 1 according to this embodiment, as described above, it is possible to scan the second scanning region V2 six times in one second and consequently acquire six volume data.

Accordingly, in this embodiment, it is possible to scan the second scanning region V2 substantially twice the times in the conventional art. Thus, a volume rate in the second scanning region V2 increases, and a three-dimensional image or an MPR image in the second scanning region V2 becomes more real-time. Therefore, a three-dimensional image or an MPR image showing a puncture needle becomes more real-time by making the puncture needle included in the second scanning region V2, and it becomes possible to check the position of the puncture needle in real time. Furthermore, according to this embodiment, by scanning the first scanning region V1, it becomes possible to make the three-dimensional image or the MPR image showing the puncture needle more real-time while acquiring and displaying a three-dimensional image or an MPR image showing a puncture object (lesion).

(Second Operation Example)

Figure 6:
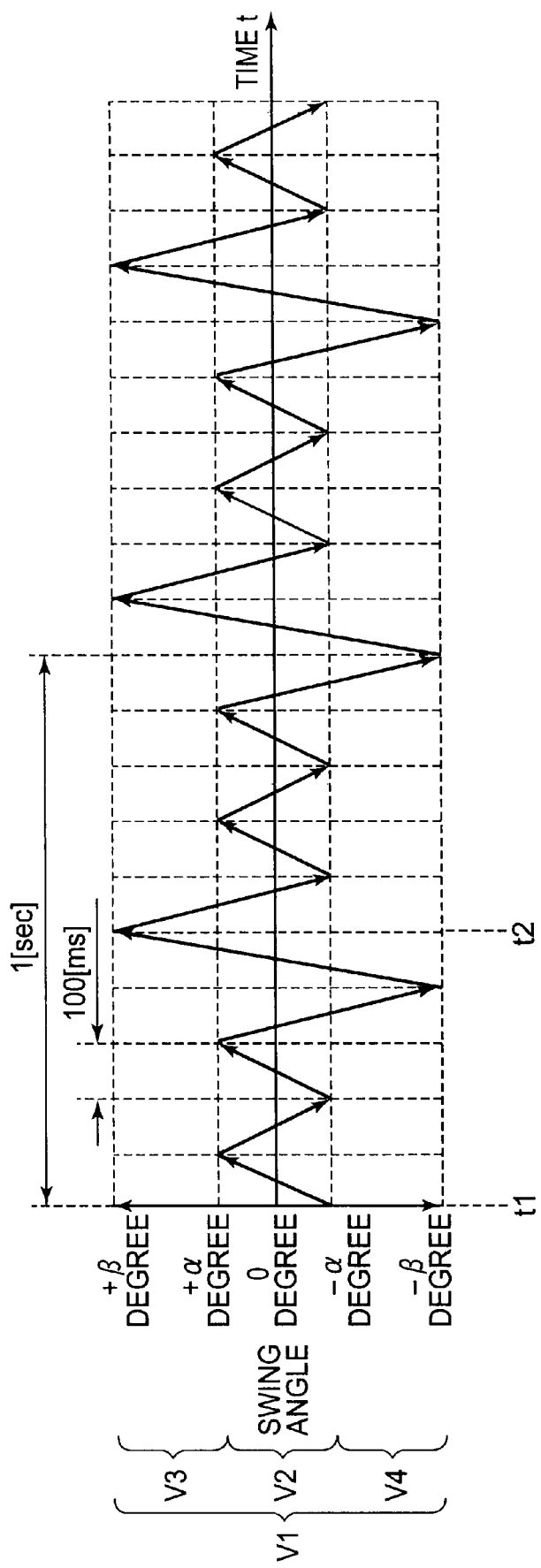
FIG. 6 is a conceptual view for explaining a second operation example of the ultrasound imaging apparatus according to the embodiment of the present invention.
Figure 7:
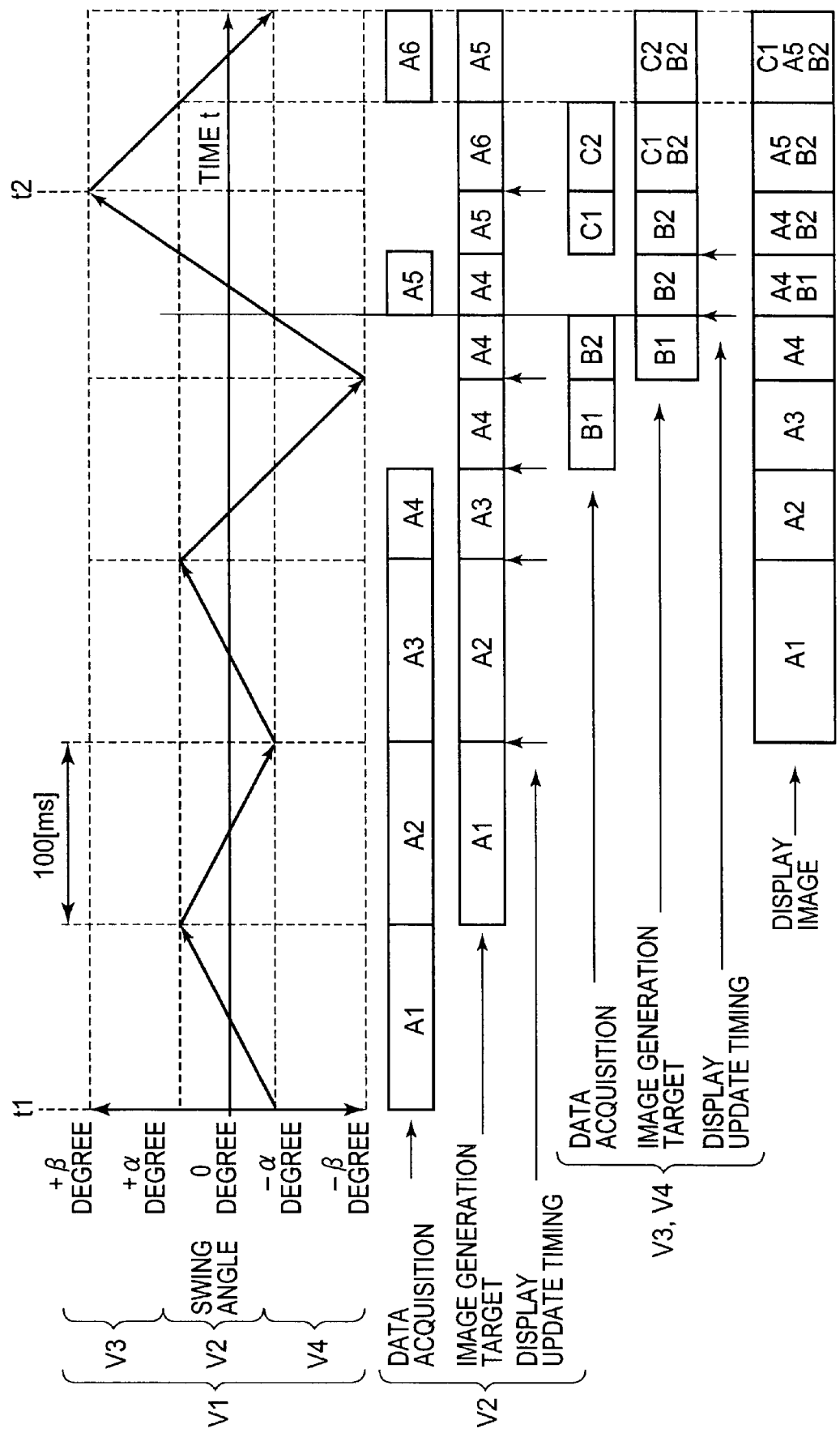
FIG. 7 is a conceptual view for explaining the second operation example of the ultrasound imaging apparatus according to the embodiment of the present invention.

Next, a second operation example will be described with reference to FIGS. 6 and 7. FIGS. 6 and 7 are conceptual views for explaining the second operation example of the ultrasound imaging apparatus according to the embodiment of the present invention. In graphs shown in FIGS. 6 and 7, the horizontal axis takes time t, and the vertical axis takes a swing angle. Further, the graph shown in FIG. 7 is a graph in which a part between time t1 and time t2 in FIG. 6 is magnified.

FIG. 7 shows the timing of data acquisition in each of the scanning regions, and data subjected to image generation and the timing for display update thereof.

In the second operation example, in swing of the group of ultrasound transducers 21, a required time from a return of a swing to a subsequent return is kept constant, and each of the scanning regions is scanned in this state. Specifically, in a state where a swing speed in a scanning region including the third scanning region V3 and the fourth scanning region V4 is kept faster than a swing speed in the second scanning region V2 including a puncture needle, each of the scanning regions is scanned.

The operator uses the operation part 82 to input, for example, a swing angle for defining each of the scanning regions (+α degree, −α degree, +β degree, −β degree), a first swing speed in the second scanning region V2, and the number of times of consecutively scanning the second scanning region V2. The swing angle information, swing speed information and number-of-times information inputted through the operation part 82 are outputted from the user interface (UI) 8 to the controller 9, and stored in the operation-condition storage 93. The controller 9 obtains a time required to scan the second scanning region V2 once, based on the first swing speed in the second scanning region V2 and the range of the second scanning region V2 (from −α degree to +α degree). In other words, a time required to swing the group of ultrasound transducers 21 from −α degree to +α degree in the second scanning region V2 is obtained. This time becomes a required time between a return and a subsequent return. In the second operation example, each of the scanning regions is scanned with this time kept constant.

Further, the operator may input a required time between a return of swing and a subsequent return by using the operation part 82. In this case, the controller 9 obtains the first swing speed in the second scanning region V2 based on the range of the second scanning region V2 and the aforementioned time.

Then, the controller 9 obtains a second swing speed at the time of consecutively scanning the second scanning region V2 and the fourth scanning region V4, based on the required time between the return of swing and the subsequent swing and based on the range (from +α degree to −β degree) including the second scanning region V2 and the fourth scanning region V4. Likewise, the controller 9 obtains a third swing speed at the time of subsequently scanning the entire first scanning region V1, based on the required time between the return of swing and the subsequent return and based on the range of the first scanning region (from −β degree to +β degree).

In the swing operation of the group of ultrasound transducers 21, if the time from the return of swing and the subsequent return is kept constant, the swing speed at the time of subsequently scanning a wider region becomes the fastest. On the other hand, the swing speed at the time of scanning a narrower scanning region becomes the slowest. In the above example, the third swing speed at the time of subsequently scanning the first scanning region V1 becomes the fastest. The second swing speed at the time of subsequently scanning the second scanning region V2 and the fourth scanning region V4 (or the third scanning region V3) becomes the second fastest. The first swing speed at the time of scanning the second scanning region V2 becomes the slowest. The first, second and third swing speeds are stored in the operation-condition storage 93 as the swing conditions. The swing controller 91 controls the group of ultrasound transducers 21 to swing in accordance with each of the swing speeds.

The control of swing using the first, second and third swing speeds will be described with reference to FIGS. 6 and 7. As shown in FIGS. 6 and 7, under the control of the controller 9, the transceiver 3 causes the group of ultrasound transducers 21 to generate an ultrasonic beam, and the scan plane S is scanned by electronic scan in the scanning direction (X direction) with the ultrasonic beam. While the electronic scan is performed, under the control of the swing controller 91, the swing mechanism 22 mechanically swings the group of ultrasound transducers 21 from −α degree to +α degree in the swing direction (Y direction) in accordance with the first swing speed. Consequently, as shown in FIG. 7, the transceiver 3 acquires the volume data A1 of the second scanning region V2, and the volume data A1 is stored into the storage 5.

Under the control of the image generation controller 92, the data acquiring part 61 acquires the volume data A1 of the second scanning region V2 acquired at the closest time, from the storage 5, and outputs the volume data to the image generator 62. The image generator 62 generates three-dimensional image data or MPR image data based on the volume data A1. The display controller 7 causes the display 81 to display a three-dimensional image or an MPR image.

Likewise, under the control of the swing controller 91, in accordance with the first wing speed, the swing mechanism 22 mechanically swings the group of ultrasound transducers 21 from +α degree to −α degree, and further mechanically swings the group of ultrasound transducers 21 from −α degree to +α degree. Consequently, the transceiver 3 sequentially acquires the volume data A2 and A3 in the second scanning region V2. The data acquiring part 61 sequentially acquires the volume data A2 and A3 from the storage 5, and outputs the volume data to the image generator 62. The image generator 62 sequentially generates three-dimensional image data or MPR image data respectively based on the volume data A2 and A3. The display controller 7 updates an image displayed on the display 81, and controls the display 81 to display a new three-dimensional image or an MPR image.

In the example shown in FIGS. 6 and 7, after controlling the group of ultrasound transducers 21 to consecutively swing three times at the first swing speed in the second scanning region V2, the swing controller 91 changes the swing speed from the first swing speed to the second swing speed and controls the group of ultrasound transducers 21 to swing from +α degree to −β degree. In other words, the swing controller 91 counts the number of swings in the second scanning region V2 and, when counting the number of times (three times) that is one time less than the set number of times (four times), the swing controller 91 changes the swing speed from the first swing speed to the second swing speed and controls the group of ultrasound transducers 21 to swing from +α degree to −β degree. Consequently, the transceiver 3 sequentially acquires the volume data A4 in the second scanning region V2 and the volume data B1 in the fourth scanning region V4. The data acquiring part 61 acquires the volume data A4 acquired at the closest time from the storage 5 with regard to the second scanning region V2, and acquires the volume data B1 from the storage 5 with regard to the fourth scanning region V4, and outputs the volume data to the image generator 62. Then, the image generator 62 combines the volume data A4 and volume data B1 to generate three-dimensional image data or MPR image data based on the combined volume data. The display controller 7 updates the image displayed on the display 81 and causes the display 81 to display a three-dimensional image or an MPR image in which the second scanning region V2 and the fourth scanning region V4 are shown.

Then, the swing controller 91 changes the swing speed from the second swing speed to the third swing speed and causes the group of ultrasound transducers 21 to swing from −β degree to +β degree. Thus, the transceiver 3 sequentially scans the fourth, second and third scanning regions V4, V2 and V3. As a result, the transceiver 3 sequentially acquires the volume data B2 in the fourth scanning region V4, the volume data A5 in the second scanning region V2, and the volume data C1 in the third scanning region V3.

At this moment, under the control of the image generation controller 92, the data acquiring part 61 acquires the volume data A4 from the storage 5 and outputs the volume data to the image generator 62 with regard to the second scanning region V2, and acquires the volume data B2 from the storage 5 and outputs the volume data to the image generator 62 with regard to the fourth scanning region V4. The image generator 62 combines the volume data A4 and the volume data B2 to generate three-dimensional image data or MPR image data based on the combined volume data. The display controller 7 updates the image displayed on the display 81 and causes the display 81 to display a new three-dimensional image or MPR image. Consequently, the three-dimensional image or the MPR image in the fourth scanning region V4 is updated and displayed on the display 81.

After that, the data acquiring part 61 acquires from the storage 5 the volume data A5 acquired at the closest time with regard to the second scanning region V2, and acquires the volume data B2 from the storage 5 with regard to the fourth scanning region V4, and outputs the volume data to the image generator 62. The image generator 62 combines the volume data A5 and the volume data B2 to generate three-dimensional image data or MPR image data based on the combined volume data. The display controller 7 updates the image displayed on the display 81 and causes the display 81 to display a new three-dimensional image or an MPR image. Consequently, the three-dimensional image or the MPR image in the second scanning region V2 including a puncture needle is updated and displayed on the display 81.

After that, the data acquiring part 61 acquires the volume data A5 from the storage 5 with regard to the second scanning region V2, acquires the volume data B2 from the storage 5 with regard to the fourth scanning region V4, and acquires, from the storage 5, the volume data C1 acquired at the closest time with regard to the third scanning region V3, and outputs the volume data to the image generator 62. The image generator 62 combines the volume data A5, the volume data B2 and the volume data C1 to generate three-dimensional image data or MPR image data based on the combined volume data. The display controller 7 updates the image displayed on the display 81 and causes the display 81 to display a three-dimensional image or an MPR image in which the second scanning region V2, the third scanning region V3 and the fourth scanning region V4 are represented. Consequently, a three-dimensional image or an MPR image in which the entire scanning region V1 is represented is displayed on the display 81. In other words, a three-dimensional image or an MPR image representing the entire image of a puncture object (lesion) is displayed on the display 81.

Then, as described in FIG. 6, under the control of the swing controller 91, the swing mechanism 22 changes the swing speed from the third swing speed to the second swing speed and causes the group of ultrasound transducers 21 to swing from +β degree to −α degree.

Consequently, the transceiver 3 sequentially scans the third scanning region V3 and the second scanning region V2. As a result, the transceiver 3 sequentially acquires volume data C2 in the third scanning region V3 and volume data A6 in the second scanning region V2.

After that, the swing controller 91 repeatedly executes the aforementioned swing sequence, whereby the swing mechanism 22 consecutively swings the group of ultrasound transducers 21 more than once at the first swing speed in the second scanning region V2. Further, in a case where the second scanning region V2 and the third scanning region V3 (or the fourth scanning region V4) are scanned, the swing mechanism 22 swings the group of ultrasound transducers 21 at the second swing speed. Further, in a case where the first scanning region V1 is scanned subsequently, the swing mechanism 22 swings the group of ultrasound transducers 21 at the first swing speed.

In the example in FIGS. 6 and 7, scan is performed assuming a required time from a return of swing to a subsequent return is 100 ms in the swing of the group of ultrasound transducers 21.

According to the second operation, as in the first operation, by consecutively scanning the second scanning region V2 more than once every time scanning the first scanning region V1 once, it becomes possible to make a three-dimensional image or an MPR image showing a puncture needle more real-time, while acquiring and displaying a three-dimensional image or an MPR image showing the entire image of a puncture object (lesion).

Furthermore, according to the second operation, the required time from the return of swing to the subsequent return is constant, so that variation in time interval during which the volume data in the second scanning region V2 is acquired becomes less, and it becomes possible to acquire the volume data with approximately the same time interval. Specifically, in the volume data A1, A2 and A3, the time intervals of data acquisition become constant. Moreover, in the volume data A3, A4 and A5, the time intervals of data acquisition become approximately constant. Thus, the volume data in the second scanning region V2 are acquired with approximately the same time intervals, and therefore, it becomes possible to update and display a three-dimensional image or an MPR image in the second scanning region V2 with approximately the same time intervals.

(Third Operation)

In the first operation mentioned above, the swing is performed at a constant swing speed. In the second operation, the swing is performed in a state where a required time from a return of swing to a subsequent return is kept constant. The swing operation by the ultrasound imaging apparatus 1 according to this embodiment is not limited to those described above. The swing speed may be changed arbitrarily, and the required time before the subsequent return may be changed arbitrarily.

For example, in the second operation, the swing may be performed in a state where the first and second swing speeds are kept to be the same and only the third swing speed is changed. In this case, the time required before the subsequent return is not kept constant, but it is possible to make a three-dimensional image or MPR image showing a puncture needle more real-time by consecutively scanning the second scanning region V2 more than once. Further, the range of each of the scanning regions may be changed. Specifically, it is possible to produce an effect according to this embodiment even if the range of the swing angle defining the second scanning region V2, the range of the swing angle defining the third scanning region V3 and the range of the swing angle defining the fourth scanning region V4 are each changed.

(Displayed Image)

Figure 8:
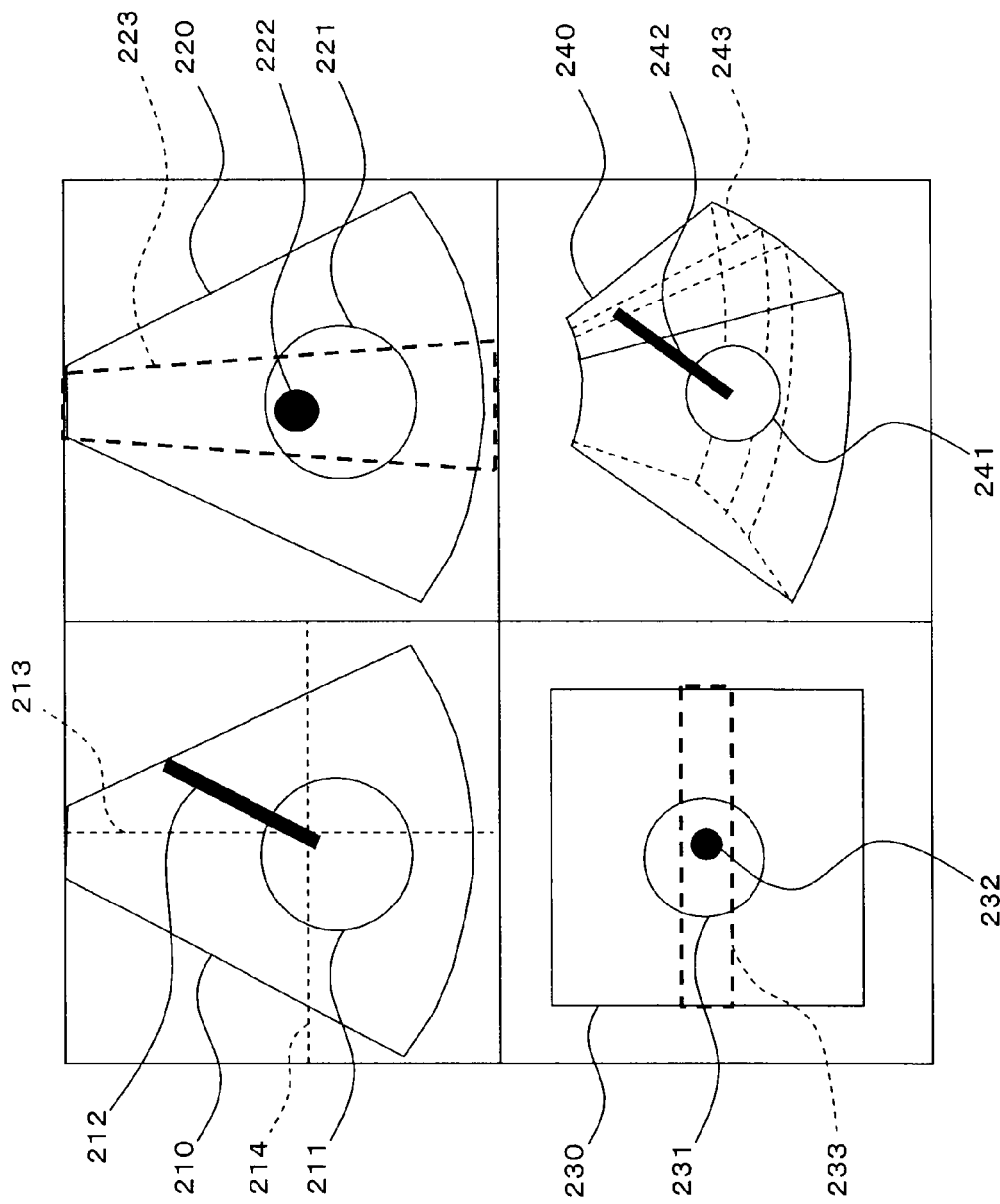
FIG. 8 is a view of a screen showing a display example of an image acquired by the ultrasound imaging apparatus according to the embodiment of the present invention.

Next, an example of a three-dimensional image or an MPR image generated by the image generator 62 and displayed on the display 81 will be described with reference to FIG. 8. FIG. 8 is a view of a screen showing a display example of an image acquired by the ultrasound imaging apparatus according to the embodiment of the present invention.

For example, the image generator 62 generates three-dimensional image data, image data taken from the swing direction (Y direction), image data taken from the scanning direction (X direction), and image data taken from the depth direction (Z direction), based on volume data in which volume data of the respective scanning regions are combined.

The display controller 7 causes the display 81 to display these images. For example, the display controller 7 causes the display 81 to simultaneously display four images.

A display example of an image is shown in FIG. 8. For example, as shown in FIG. 8, the display controller 7 causes the display 81 to display a three-dimensional image 240 in which a puncture object 241 and a puncture needle 242 are represented in three dimension. In this three-dimensional image 240, a region 243 indicated by a broken line corresponds to the second scanning region V2. Further, the display controller 7 causes the display 81 to simultaneously display images 210, 220 and 230. The image 210 is an MPR image taken from the swing direction (Y direction), and corresponds to an image at a cross-section along the scan plane S in the second scanning region V2. In this image 210, the puncture object 211 and the puncture needle 212 taken from the swing direction are represented. Further, the image 220 is an MPR image taken from the scanning direction (X direction) in which the puncture object 221 and the puncture needle 222 taken from the scanning direction are represented. In this image 220, a region 223 indicated by a broken line corresponds to the second scanning region V2.

Further, the image 230 is an MPR image taken from the depth direction (Z direction), in which the puncture object 231 and the puncture needle 232 taken from the depth direction are represented. In this image 230, a region 233 indicated by a broken line corresponds to the second scanning region V2.

The image 210 is an MPR image taken from the swing direction (Y direction) and is an image at a cross-section along the scan plane S in the second scanning region V2. Therefore, the image 210 includes only an image in the second scanning region V2. On the other hand, the image 220 is an MPR image taken from the scanning direction (X direction), and the image 230 is an MPR image taken from the depth direction (Z direction). Therefore, the image 220 and the image 230 include an image in the second scanning region V2 for the puncture needle and the other images in the third scanning region V3 and the fourth scanning region V4. Moreover, the display controller 7 may receive coordinate information indicating the position of the cross-section of the image 220 and cause the display 81 to display a line 213 indicating the position of the cross-section of the image 220 in the overlapping state with the image 210. Likewise, the display controller 7 may receive coordinate information indicating the position of the cross-section of the image 230 and cause the display 81 to display a line 214 indicating the position of the cross-section of the image 230 in the overlapping state with the image 210.

The images 210, 220 and 230 may be MIP images, MIP images with thickness or MPR images with thickness, other than the MPR images. Moreover, the image shown in FIG. 8 is an example, and it is also possible to display only an image taken from a desired direction without displaying the four images on the display 81.

Further, the operator may observe an image displayed on the display 81 and designate the range of the second scanning region V2 by using the operation part 82 so that the puncture needle is included in the second scanning region V2. Specifically, the operator inputs the range of a swing angle defining the second scanning region V2 through the operation part 82. The swing angle information inputted through the operation part 82 is outputted from the user interface (UI) 8 to the controller 9 and is stored in the operation-condition storage 93 as the swing condition. The swing controller 91 controls the swing of the group of ultrasound transducers 21 in accordance with the newly set swing condition. Thus, by arbitrarily changing the range of the second scanning region V2 while performing puncture, it becomes possible to perform scan in a state where the puncture needle is included in the second scanning region V2 even if the position of the puncture needle moves off the second scanning region V2.

A three-dimensional scanning region is scanned with ultrasonic waves so as to include a puncture object (lesion), and a three-dimensional image representing the entire image is displayed on the display 81 in order to set the second scanning region V2. The operator observes the three-dimensional image displayed on the display 81 and designates the first scanning region V1 and the second scanning region V2 by using the operation part 82. More specifically, the operator inputs, via the operation part 82, the range of the swing angle of the first scanning region V1 and the range of the swing angle of the second scanning region V2 while observing the three-dimensional image.

The operator may input, via the operation part 82, the range of the swing angle of the second scanning region V2, the range of the swing angle of the third scanning region V3, and the range of the swing angle of the fourth scanning region V4.

(Modification)

Next, a modification of the ultrasound imaging apparatus 1 will be described. In the embodiment described above, a mechanical 1D array probe is used as the ultrasound probe 2, and a three-dimensional scanning region is scanned by controlling the swing of the group of ultrasound transducers 21. As the modification, it is possible to by use a 2D array probe as the ultrasound probe 2 and consecutively scan the second scanning region V2 more than once every time the first scanning region V1 is scanned once.

For example, as shown in FIG. 5, under the control of the controller 9, the transceiver 3 consecutively acquires volume data in the second scanning region V2 four times by consecutively scanning the second scanning region V2 four times. After that, the transceiver 3 acquires volume data in the first scanning region V1 by scanning the first scanning region V1 once. Thus, even if a 2D array probe is used, by consecutively scanning the second scanning region V2 more than once every time the first scanning region V1 is scanned once, it becomes possible to make a three-dimensional image or an MPR image representing a puncture needle more real-time while acquiring and displaying a three-dimensional image or an MPR image representing the entire image of a puncture object (lesion).

Moreover, in this embodiment, the image generator 62 combines volume data in the respective scanning regions and generates three-dimensional image data or MPR image data based on the combined volume data. The combining method is an example, so it is possible to combine three-dimensional image data or MPR image data without combining the volume data. For example, the image generator 62 may generate three-dimensional image data representing each of the scanning regions by executing volume rendering on the volume data in each of the scanning regions. Then, the image generator 62 generates three-dimensional image data representing the whole by combining three-dimensional image data in each of the scanning regions. The display controller 7 causes the display 81 to display a three-dimensional image based on the three-dimensional image data representing the whole.

When volume data in each of the scanning regions is newly acquired, the image generator 62 generates three-dimensional image data in the scanning region based on the volume data in the scanning region. Then, the image generator 62 combines the three-dimensional image data in the scanning region and three-dimensional image data in other scanning region to generate three-dimensional image data representing the whole. Thus, it is possible to produce the same effect as in the aforementioned embodiment even if the image data after rendering are combined. Furthermore, the display controller 7 may put three-dimensional images in the respective scanning regions together and control the display 81 to display them.

(Modification 2)

Figure 9:
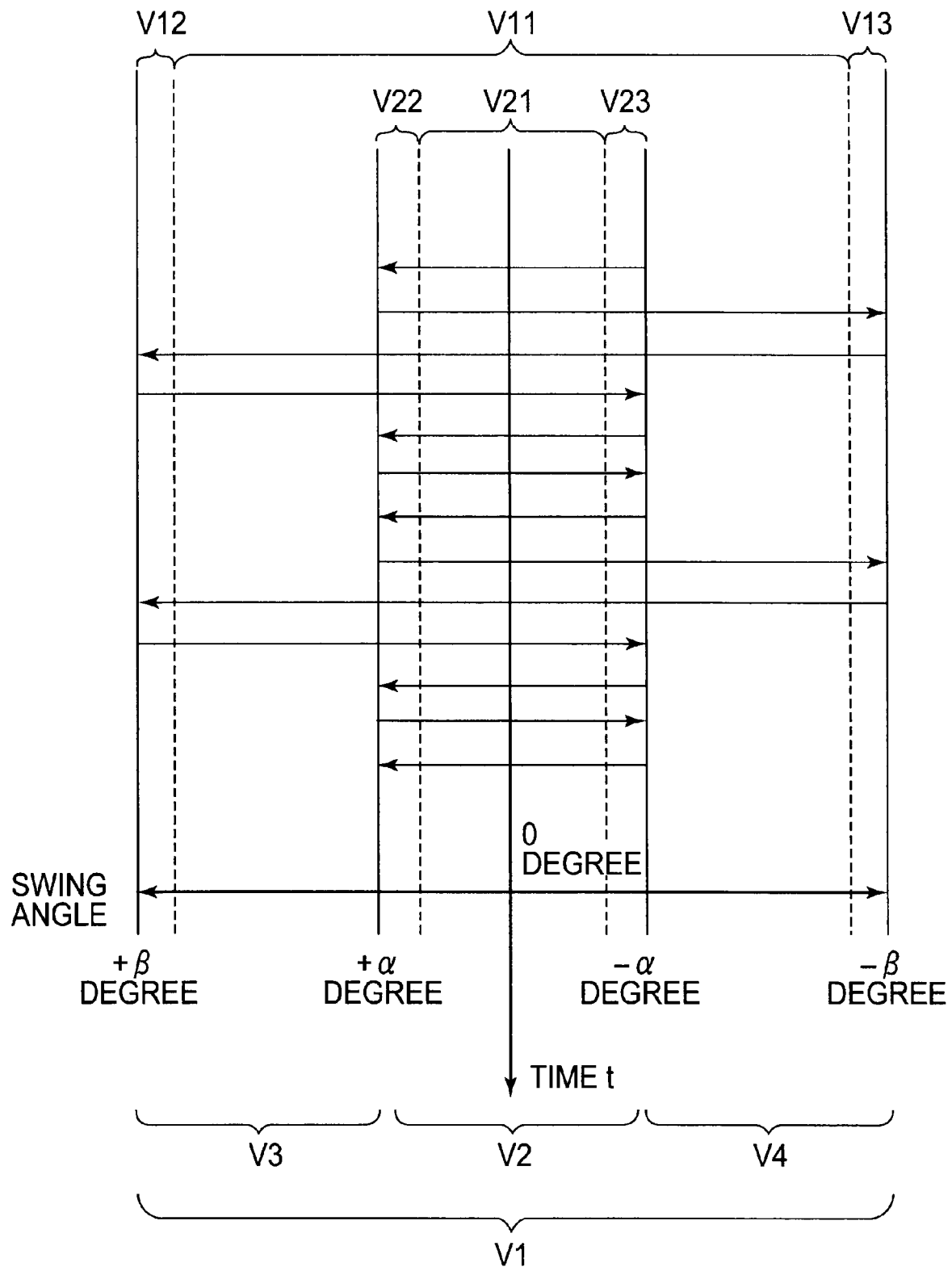
FIG. 9 is a conceptual view showing a scanning region and an image-generating region.

Next, Modification 2 of the ultrasound imaging apparatus 1 will be described with reference to FIG. 9. FIG. 9 is a conceptual view showing a scanning region and an image-generating region. In the modification 2, a region that is narrower than the scanning region and is included in the scanning region will be an image-generating region, and three-dimensional image data or MPR image data in the image-generating region is generated. In other words, a region that is within the scanning region and is narrower than the scanning region will be an image-generating region.

In the case of swinging the group of ultrasound transducers 21 in each of the scanning regions, it is necessary to make the group of ultrasound transducers 21 return at the boundary of the scanning regions.

Therefore, it is necessary to accelerate or decelerate the group of ultrasound transducers 21 in the vicinity of the boundary of the scanning regions (in the vicinity of the return position in the swing operation). For example, in the case of swinging the group of ultrasound transducers 21 in the second scanning region V2, it is necessary to accelerate or decelerate the group of ultrasound transducers 21 around the boundary of the second scanning region V2 (around +α degree, or around −α degree). Thus, it is necessary to accelerate or decelerate the group of ultrasound transducers 21 around the return position in the swing operation.

In the example shown in FIG. 9, boundary regions V22 and V23 of the second scanning regions correspond to regions in the vicinity of the returning position of the swing operation of the group of ultrasound transducers 21. In other words, the regions V22 and V23 correspond to a region in which the group of ultrasound transducers 21 is accelerated or a region in which the group of ultrasound transducers 21 is decelerated.

Likewise, boundary regions V12 and V13 of the first scanning region V1 correspond to a region in the vicinity of the return position in a swing operation of the group of ultrasound transducers 21. In other words, the regions V12 and V13 correspond to a region in which the group of ultrasound transducers 21 is accelerated or a region in which the group of ultrasound transducers 21 is decelerated.

Thus, the return of the swing operation of the group of ultrasound transducers 21 is performed at the boundary of the first scanning region V1 and at the boundary of the second scanning region V2. Therefore, the swing speed of the group of ultrasound transducers 21 is not constant in the vicinity of the boundary of the first scanning region V1 or in the vicinity of the boundary of the second scanning region V2. In other words, in the vicinity of the boundary of the first scanning region V1 and the vicinity of the boundary of the second scanning region V2, a volume rate changes every moment and the volume rate is not kept constant. Thus, in the vicinity of boundary of the first scanning region V1 and in the vicinity of the boundary of the second scanning region V2, the volume rate is not kept constant, and the quality of images acquired in the vicinity of the boundary varies depending on the place. Further, the image quality is different between images acquired in the vicinity of the return position of the swing operation and images acquired in other regions where the swing speed is constant.

Therefore, in the modification 2, a region that is narrower than the scanning region and is included in the scanning region will be an image-generating region, and image data in the image-generating region will be generated. As an example, a region obtained by excluding a region where the group of ultrasound transducers 21 is accelerated or decelerated from the scanning region will be an image-generating region.

In other words, a region obtained by excluding a region in the vicinity of the return position of the swing operation of the group of ultrasound transducers 21 from the scanning region is regarded as an image-generating region.

In the example shown in FIG. 9, the region V11 obtained by excluding the region V12 and the region V13 from the first scanning region V1 is regarded as a first image-generating region. Furthermore, a region V21 obtained by excluding the region V22 and region V23 from the second scanning region V2 is regarded as a second image-generating region. Consequently, the first image-generating region V11 is included in the first scanning region V1, and is set more toward the inside than is the first scanning region V1. Moreover, the second image-generating region V21 is included in the second scanning region V2 and is set more inside than is the second scanning region V2.

Image generation information indicating the range of an angle for defining an image-generating region is stored in the operation-condition storage 93. More specifically, image generation information indicating the range of an angle for defining the first image-generating region V11 and image generation information indicating the range of an angle for defining the second image-generating region V21 are stored in the operation-condition storage 93.

The image generation controller 92 outputs, to the data acquiring part 61, the swing angle information, the time information, and the image generation information. Further, the data acquiring part 61 outputs the image generation information to the image generator 62.

For example, when volume data in the second scanning region V2 is acquired, in accordance with the swing angle information indicating the range of the second scanning region V2 and the time information outputted from the image generation controller 92, the data acquiring part 61 acquires, from the storage 5, the volume data in the second scanning region V2 acquired at the closest time, and outputs the volume data to the image generator 62.

Based on the volume data in the second scanning region V2, the image generator 62 generates three-dimensional image data or MPR image data in the second image-generating region V21 indicated by the image generation information. Consequently, image data in the second image-generating region V21 is generated, excluding a region where the group of ultrasound transducers 21 is accelerated or decelerated. In other words, image data in the second image-generating region V21 is generated, excluding a region in the vicinity of the return position of the swing operation of the group of ultrasound transducers 21.

Further, in the case of generating image data in the first scanning region V1 by combining volume data in the respective scanning regions, the image generator 62 also generates image data in the first image-generating region V11, excluding the region where the group of ultrasound transducers 21 is accelerated or decelerated. More specifically, the image generator 62 generates three-dimensional image data or MPR image data in the first image-generating region V11 indicated by the image generation information, based on the volume data in the first scanning region V1. Consequently, excluding the region in the vicinity of the return position of the swing operation of the group of ultrasound transducers 21 (the accelerating region or the decelerating region), the image data in the first image-generating region V11 is generated.

Accordingly, by setting the image-generating region inside the scanning region, it is possible to set the image-generating region while avoiding a region to accelerate or decelerate the group of ultrasound transducers 21 (a region in the vicinity of the return position of the swing operation). By generating image data in the image-generating region, it is possible to generate the image data while avoiding a region where a volume rate changes every moment.

The operator may use the operation part 82 to input image generation information indicating the range of an image generation angle. The image generation information inputted through the operation part 82 is outputted from the user interface (UI) to the controller 9, and is stored into the operation-condition storage 93 of the controller 9.

What is claimed is:

1. An ultrasound imaging apparatus, comprising:
an ultrasound probe configured to scan a three-dimensional scanning region to acquire volume data in the scanning region;
a controller configured to control the ultrasound probe to scan a three-dimensional first scanning region to acquire first volume data in the entire first scanning region, and control the ultrasound probe to consecutively scan a second scanning region more than once to consecutively acquire second volume data in the entire second scanning region, the second scanning region being smaller than the first scanning region and included in the first scanning region, wherein the controller is configured to control the ultrasound probe so that the scanning of the second scanning region starts after an end of the scanning of the entire first scanning region, and a next scanning of the entire first scanning region starts after an end of the scanning of the second scanning region, wherein each scanning of the entire first scanning region includes scanning the second scanning region only once and is conducted with a same scanning resolution as the scanning of the second scanning region, independent from the first scanning region;
an image generator configured to generate ultrasound image data in the first scanning region including the second scanning region based on the first volume data in the first scanning region and, every time the second volume data in the second scanning region is acquired by consecutively scanning more than once, update the second volume data in the second scanning region to generate new ultrasound image data; and
a display controller configured to control a display to display an ultrasound image based on the generated ultrasound image data and, every time the new ultrasound image data is generated, update the ultrasound image displayed on the display to control the display to display the ultrasound image.

2. The ultrasound imaging apparatus according to claim 1, wherein:
the controller is configured to control the ultrasound probe to consecutively scan the second scanning region more than once, every time the first scanning region is scanned once.

3. The ultrasound imaging apparatus according to claim 1, wherein:
the ultrasound probe includes a group of ultrasound transducers including a plurality of ultrasound transducers arranged in a row in a predetermined direction, a swing mechanism configured to swing the group of ultrasound transducers in a swing direction orthogonal to the predetermined direction, and a transceiver configured to transmit and receive ultrasonic waves to and from the group of ultrasound transducers and thereby scan a scan plane along the predetermined direction with the ultrasonic waves, wherein the swing mechanism includes a motor;
the swing mechanism is configured to swing the group of ultrasound transducers in the swing direction while the transceiver scans the scan plane with the ultrasonic waves, and the volume data in the scanning region is thereby acquired; and the controller is configured to control the swing mechanism to swing the group of ultrasound transducers within a range of a first swing angle corresponding to the first scanning region, thereby controlling the ultrasound probe to acquire the first volume data in the first scanning region, and the controller is configured to control the swing mechanism to consecutively swing the group of ultrasound transducers more than once within a range of a second swing angle that corresponds to the second scanning region and that is smaller than the first swing angle, thereby controlling the ultrasound probe to consecutively acquire the second volume data in the second scanning region.

4. The ultrasound imaging apparatus according to claim 3, wherein:

the controller is configured to control the group of ultrasound transducers to swing while making a swing speed in the swing direction of the group of ultrasound transducers within the first scanning region equal to a swing speed in the swing direction of the group of ultrasound transducers within the second scanning region.

5. The ultrasound imaging apparatus according to claim 3, wherein:

the controller is configured to control the group of ultrasound transducers to swing while making a swing speed in the swing direction of the group of ultrasound transducers within the first scanning region faster than a swing speed in the swing direction of the group of ultrasound transducers within the second scanning region.

6. The ultrasound imaging apparatus according to claim 3, wherein:

the controller is configured to control the group of ultrasound transducers to swing within the range of the first swing angle so that a substantially central range in the swing direction within the range of the first swing angle is the range of the second swing angle; and every time the second volume data in the second scanning region or volume data in a region within the first scanning region, but outside the second scanning region, is acquired by the ultrasound probe, the image generator updates the volume data in each of the regions and generates the new ultrasound image data.

7. The ultrasound imaging apparatus according to claim 1, wherein:

the image generator is configured to generate ultrasound image data in a second image-generating region that is smaller than the second scanning region and that is included in the second scanning region based on the second volume data in the second scanning region, and generate ultrasound image data in a first image-generating region that is smaller than the first scanning region and that is included in the first scanning region based on the first volume data in the first scanning region.

8. The ultrasound imaging apparatus according to claim 3, wherein:

the image generator is configured to generate ultrasound image data in an image-generating region, which is a region excluding a region around an edge region of a swing operation of the group of ultrasound transducers, within the first scanning region and the second scanning region.

9. The ultrasound imaging apparatus of claim 1, wherein when a puncture object and a puncture needle are scanned, the controller is configured to control the ultrasound probe to scan the second scanning region so as to include the puncture needle.

10. A method for generating an ultrasound image, comprising:

scanning a three-dimensional first scanning region with ultrasonic waves, and acquiring first volume data in the entire first scanning region;

consecutively scanning a second scanning region that is smaller than the first scanning region and that is included in the first scanning region with ultrasonic waves more than once, and consecutively acquiring second volume data in the entire second scanning region, wherein the scanning of the second scanning region starts after an end of the scanning of the entire first scanning region, and a next scanning of the entire first scanning region starts after an end of the scanning of the second scanning region, wherein each scanning of the entire first scanning region includes scanning the second scanning region only once, and is conducted with a same scanning resolution as the scanning of the second scanning region, independent from the first scanning region;

generating ultrasound image data in the first scanning region including the second scanning region based on the first volume data in the first scanning region and, every time the second volume data in the second scanning region is acquired by consecutive scan more than once, updating the second volume data in the second scanning region and generating new ultrasound image data; and displaying an ultrasound image based on the generated ultrasound image data and, every time the new ultrasound image data is generated, updating the displayed ultrasound image and displaying.

11. The method for generating an ultrasound image according to claim 10, wherein:

every time the first scanning region is scanned once, the second scanning region is consecutively scanned more than once.

12. The method for generating an ultrasound image according to claim 10, wherein:

the step of scanning the first scanning region includes swinging a group of ultrasound transducers, which includes a plurality of ultrasound transducers arranged in a row in a predetermined direction and scans a scan plane along the predetermined direction with ultrasonic waves, in a swing direction orthogonal to the predetermined direction within a range of a first swing angle corresponding to the first scanning region, and the first volume data in the first scanning region is thereby acquired; and the step of consecutively scanning the second scanning region includes consecutively swinging the group of ultrasound transducers more than once within a range of a second swing angle that corresponds to the second scanning region and is smaller than the first swing angle, and the second volume data in the second scanning region is thereby acquired.

13. The method for generating an ultrasound image according to claim 12, wherein:

the group of ultrasound transducers is swung while a swing speed in the swing direction of the group of ultrasound transducers within the first scanning region is made to be equal to a swing speed in the swing direction of the group of ultrasound transducers within the second scanning region.

14. The method for generating an ultrasound image according to claim 12, wherein:
the group of ultrasound transducers is swung while a swing speed in the swing direction of the group of ultrasound transducers within the first scanning region is made to be faster than a swing speed in the swing direction of the group of ultrasound transducers within the second scanning region.

15. The method for generating an ultrasound image according to claim 12, wherein:
the group of ultrasound transducers is swung within the range of the first swing angle so that a substantially central range in the swing direction within the range of the first swing angle is the range of the second swing angle; and
every time the second volume data in the second scanning region or volume data in a region within the first scanning region, but outside the second scanning region is acquired, the volume data in each of the regions is updated and the new ultrasound image data is generated.

16. The method for generating an ultrasound image according to claim 10, wherein the generating step comprises:
generating ultrasound image data in a second image-generating region that is smaller than the second scanning region and is included in the second scanning region based on the second volume data in the second scanning region, and generating ultrasound image data in a first image-generating region that is smaller than the first scanning region and that is included in the first-scanning region based on the first volume data in the first scanning region.

17. The method for generating an ultrasound image according to claim 12, wherein the generating step comprises:
generating ultrasound image data in an image-generating region, which is a region excluding a region around an edge portion of a swing operation of the group of ultrasound transducers within the first scanning region and the second scanning region.

\* \* \* \* \*